United States Patent
Yanagihara et al.

(10) Patent No.: US 12,336,834 B2
(45) Date of Patent: Jun. 24, 2025

(54) EXAMINATION DEVICE, ENDOSCOPE SYSTEM, AND EXAMINATION METHOD

(71) Applicant: OLYMPUS CORPORATION, Tokyo (JP)

(72) Inventors: Erika Yanagihara, Chofu (JP); Ryosuke Sakurai, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 138 days.

(21) Appl. No.: 18/094,508

(22) Filed: Jan. 9, 2023

(65) Prior Publication Data

US 2023/0157623 A1  May 25, 2023

Related U.S. Application Data

(63) Continuation of application No. PCT/JP2020/027360, filed on Jul. 14, 2020.

(51) Int. Cl.
*A61B 5/00* (2006.01)
*A61B 1/273* (2006.01)
*A61B 5/103* (2006.01)
*G06T 7/00* (2017.01)

(52) U.S. Cl.
CPC .......... *A61B 5/4205* (2013.01); *A61B 1/2733* (2013.01); *A61B 5/1032* (2013.01); *A61B 5/742* (2013.01); *A61B 5/749* (2013.01); *G06T 7/0012* (2013.01); *G06T 2207/10016* (2013.01);

(Continued)

(58) Field of Classification Search
CPC ..... A61B 5/4205; A61B 1/2733; A61B 1/273; A61B 1/233; A61B 5/1032; A61B 5/742; G06T 2207/10016; G06T 2207/10024
See application file for complete search history.

(56) References Cited

U.S. PATENT DOCUMENTS 5,024,240 A * 6/1991 McConnel ........... A61B 5/4205
                                                   600/593
6,050,938 A * 4/2000 Creed ................ A61B 1/00108
                                                   600/101

(Continued)

FOREIGN PATENT DOCUMENTS

JP    2008500822 A    1/2008
JP    2011212231 A   10/2011

(Continued)

OTHER PUBLICATIONS

Mohammed ["Deep-STRESS Capsule Video Endoscopy Image Enhancement", 26th Color and Imaging Conference Final Program and Proceedings, 2018 ]. (Year: 2018).*

(Continued)

*Primary Examiner* — Oommen Jacob
(74) *Attorney, Agent, or Firm* — Scully, Scott, Murphy & Presser, P.C.

(57) ABSTRACT

An examination device includes a processor, and the processor detects, in swallowing videoendoscopy in which an inflow object is given to a subject and a swallowing action is observed, at least two timings among a swallowing instruction timing at which a swallowing instruction is given, an inflow timing of the inflow object into the pharynx during the swallowing action, and a swallowing reflex triggering timing in the subject.

20 Claims, 20 Drawing Sheets

(52) U.S. Cl.
CPC ............... *G06T 2207/10024* (2013.01); *G06T 2207/10068* (2013.01); *G06T 2207/30004* (2013.01)

(56) References Cited

U.S. PATENT DOCUMENTS

| | | | | |
|---|---|---|---|---|
| 6,878,106 | B1* | 4/2005 | Herrmann | A61B 1/267 600/128 |
| 7,734,351 | B2* | 6/2010 | Testerman | A61N 1/36007 607/48 |
| 7,775,977 | B2* | 8/2010 | Kawashima | A61B 8/12 600/443 |
| 8,092,433 | B2* | 1/2012 | Hamdy | A61N 1/36007 604/21 |
| 9,138,171 | B2* | 9/2015 | Chau | A61B 5/11 |
| 2004/0225223 | A1* | 11/2004 | Honda | A61B 1/04 128/920 |
| 2006/0169294 | A1* | 8/2006 | Kaler | A61B 5/073 128/903 |
| 2006/0293558 | A1* | 12/2006 | De Groen | G06T 7/0012 600/101 |
| 2008/0147142 | A1* | 6/2008 | Testerman | A61N 1/36007 607/48 |
| 2009/0030346 | A1* | 1/2009 | Kojima | A61B 5/4205 600/590 |
| 2009/0227907 | A1* | 9/2009 | Kandori | A61B 5/1126 600/593 |
| 2010/0261963 | A1* | 10/2010 | Yoshizawa | A61B 5/073 600/117 |
| 2012/0050451 | A1* | 3/2012 | Yan | H04N 7/147 348/14.02 |
| 2012/0089045 | A1* | 4/2012 | Seidl | A61B 5/4205 600/547 |
| 2013/0197321 | A1* | 8/2013 | Wilson | A61B 7/003 607/42 |
| 2014/0004045 | A1* | 1/2014 | Mendenhall | A61K 47/00 426/531 |
| 2014/0228714 | A1* | 8/2014 | Chau | A61B 5/7267 600/593 |
| 2014/0343415 | A1* | 11/2014 | Hoffman | A61B 6/485 600/431 |
| 2015/0260700 | A1* | 9/2015 | Dufresne | A61B 5/4205 426/231 |
| 2016/0120798 | A1 | 5/2016 | Megiddo | |
| 2016/0235353 | A1* | 8/2016 | Nakar | A61B 7/008 |
| 2017/0027495 | A1 | 2/2017 | Jedwab et al. | |
| 2017/0337684 | A1* | 11/2017 | Bradley | A61B 1/00009 |
| 2019/0029588 | A1* | 1/2019 | Weffers-Albu | A61B 5/11 |
| 2020/0022639 | A1* | 1/2020 | Shimuta | A61B 5/11 |
| 2020/0060604 | A1* | 2/2020 | Mohammadi | A61B 5/6822 |
| 2023/0157623 | A1* | 5/2023 | Yanagihara | A61B 1/07 600/476 |
| 2023/0293091 | A1* | 9/2023 | Karube | A61B 7/003 600/408 |

FOREIGN PATENT DOCUMENTS

| | | | |
|---|---|---|---|
| JP | 2011232715 A | 11/2011 | |
| JP | 2013111125 A | 6/2013 | |
| JP | 2016518403 A | 6/2016 | |
| JP | 2017510368 A | 4/2017 | |
| JP | 2017086685 A | 5/2017 | |
| JP | 6373674 B2 | 8/2018 | |
| WO | WO-2005117617 A1 * | 12/2005 | ............. A23L 19/09 |
| WO | 2014181333 A2 | 11/2014 | |
| WO | 2015154960 A1 | 10/2015 | |

OTHER PUBLICATIONS

Furuya [Identifying the Timing of Swallowing Sounds Using Videoendoscopy Findings in Healthy Adults, The Showa University Journal of Medical Sciences, 2015 vol. 27 Issue 4 pp. 271-284] . (Year: 2015).*

International Search Report dated Sep. 29, 2020 issued in PCT/JP2020/027360.

* cited by examiner

ORAL PHASE

PHARYNGEAL PHASE

FIG. 8
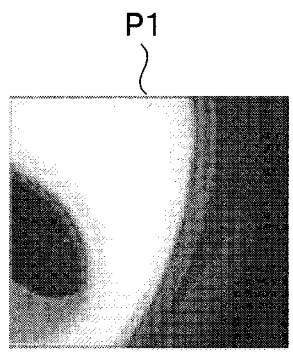
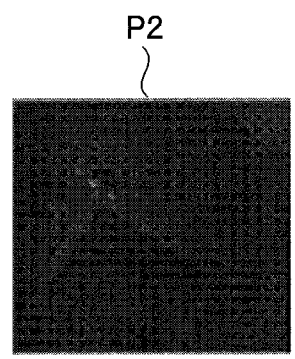
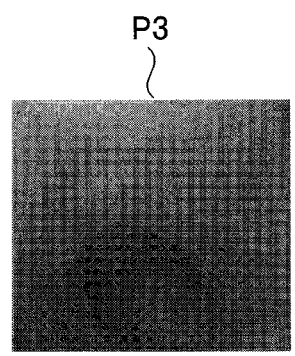

FIG. 9
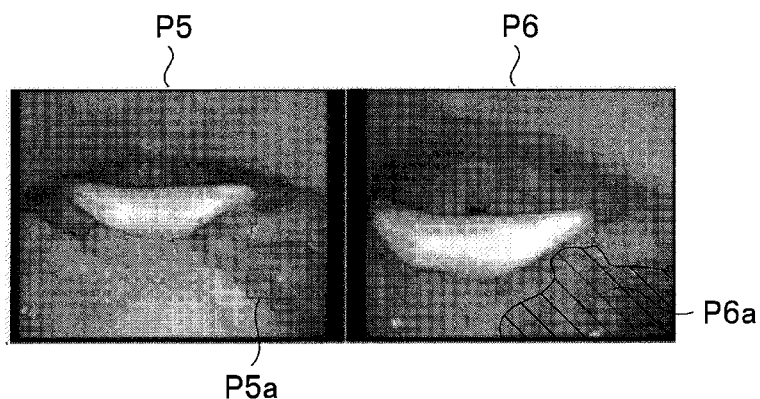
FIG. 10
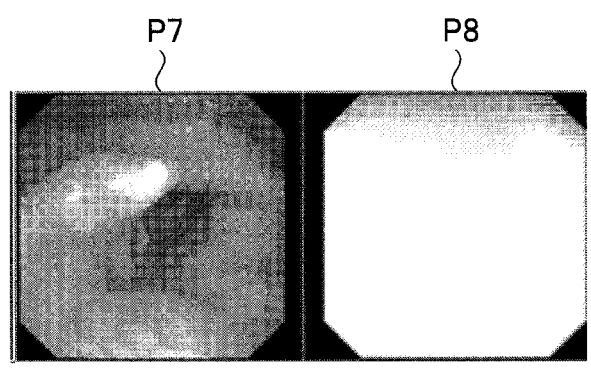
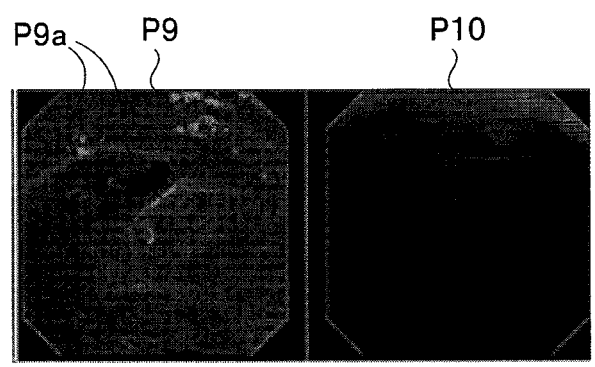

DISORDER LEVEL: SEVERE ⇒ t11 OR t11' IS APPROXIMATELY SEVERAL TENS OF SECONDS
DISORDER LEVEL: MODERATE ⇒ t11 OR t11' IS APPROXIMATELY SEVERAL SECONDS
DISORDER LEVEL: MILD ⇒ t11 OR t11' IS APPROXIMATELY 1 TO 2 SECONDS

FIG. 13

| DETERMINATION REFERENCE TIME | PHARYNGEAL SWALLOWING DISORDER | | SWALLOWING REFLEX DISORDER | | INFLOW OBJECT RESIDUAL DISORDER | |
|---|---|---|---|---|---|---|
| | EASY TO SWALLOW | DIFFICULT TO SWALLOW | EASY TO SWALLOW | DIFFICULT TO SWALLOW | EASY TO SWALLOW | DIFFICULT TO SWALLOW |
| APPROXIMATELY TENS OF SECONDS | SEVERE | MODERATE | SEVERE | MODERATE | SEVERE | MODERATE |
| APPROXIMATELY SEVERAL SECONDS | MODERATE | MILD | MODERATE | MILD | MODERATE | MILD |
| APPROXIMATELY 1 TO 2 SECONDS | MILD | MILD | MILD | MILD | MILD | MILD |

INFLOW OBJECT DIFFICULT TO SWALLOW

· INHOMOGENEOUS
· TENDING TO BREAK APART IN MOUTH
· TENDING TO STICK TO MUCOUS MEMBRANES
⇒ RICE GRUEL AND GENERAL FOOD

INFLOW OBJECT EASY TO SWALLOW

· HOMOGENEOUS
· NOT BREAKING APART IN MOUTH
· NOT STICKING TO MUCOUS MEMBRANES
⇒ THICKENED WATER AND JELLY

DISORDER LEVEL: SEVERE⇒t12 IS APPROXIMATELY SEVERAL TENS OF SECONDS
DISORDER LEVEL: MODERATE⇒t12 IS APPROXIMATELY SEVERAL SECONDS
DISORDER LEVEL: MILD⇒t12 IS APPROXIMATELY 1 TO 2 SECONDS

DISORDER LEVEL: SEVERE⇒t13 IS APPROXIMATELY SEVERAL TENS OF SECONDS
DISORDER LEVEL: MODERATE⇒t13 IS APPROXIMATELY SEVERAL SECONDS
DISORDER LEVEL: MILD⇒t13 IS APPROXIMATELY 1 TO 2 SECONDS

EXAMINATION DEVICE, ENDOSCOPE SYSTEM, AND EXAMINATION METHOD

CROSS REFERENCE TO RELATED APPLICATION

This application is a continuation application of PCT/JP2020/027360 filed on Jul. 14, 2020, the entire contents of which are incorporated herein by this reference.

BACKGROUND OF THE INVENTION

1. Field of the Invention

The present invention relates to an examination device, an endoscope system, and an examination method that effectively support swallowing videoendoscopy.

2. Description of the Related Art

A nasal endoscope inserted into the nose has been used to examine dysphagia. Dysphagia is a disorder that occurs in a series of processes in which food is sent from the mouth to the esophagus, and causes aspiration pneumonia or the like in which food enters the trachea and causes inflammation. In the swallowing videoendoscopy, a series of swallowing images is picked up after putting food for examination in the mouth using a nasal endoscope, and the picked-up images are used to determine dysphagia.

However, a swallowing reflex is an action in a moment that makes diagnosis of a disorder level relatively difficult. For this reason, it is recommended that a system for performing swallowing videoendoscopy be provided with a recording and playback function. When diagnosis by normal playback of a recorded movie is difficult, the diagnosis can be made with slow playback or frame-by-frame playback.

In Japanese Patent Application Laid-Open Publication No. 2011-232715, a technique is proposed for accurately detecting an abnormal area from an intraluminal image by creating a closed region based on gradient information on each pixel based on a pixel value of the intraluminal image and detecting the abnormal area from inside the closed region. In Japanese Patent Application Laid-Open Publication No. 2013-111125, a technique is proposed for properly detecting an abnormal area by detecting an abnormal candidate area and a tubular area from an intraluminal image of a subject, and distinguishing the abnormal area from blood vessels based on a determination result of whether the abnormal candidate area and the tubular area are connected by an area having a color similar to that of the tubular area.

SUMMARY OF THE INVENTION

According to an aspect of the present invention, an examination device includes a processor, and the processor detects, in swallowing videoendoscopy in which an inflow object is given to a subject and a swallowing action is observed, at least two timings among a swallowing instruction timing at which a swallowing instruction is given, an inflow timing of the inflow object into the pharynx during the swallowing action, and a swallowing reflex triggering timing in the subject.

According to another aspect of the present invention, an endoscope system includes an endoscope, in swallowing videoendoscopy in which an inflow object is given to a subject and a swallowing action is observed, configured to be inserted into the subject, pick up images of the pharynx, and output the images picked up, a microphone configured to collect a voice of an operator, and a processor, in which the processor detects a swallowing instruction timing at which the operator instructs swallowing based on the voice from the microphone, and detects an inflow timing of the inflow object into the pharynx during the swallowing action and a swallowing reflex triggering timing in the subject based on the images picked up, and determines dysphagia of the subject based on information on at least two timings detected.

According to an aspect of the present invention, an examination method includes detecting, in swallowing videoendoscopy in which an inflow object is given to a subject and a swallowing action is observed, at least two timings among a swallowing instruction timing instructed to swallow by an operator, an inflow timing of the inflow object into the pharynx during the swallowing action, and a swallowing reflex triggering timing in the subject.

BRIEF DESCRIPTION OF THE DRAWINGS

FIG. 8 is an explanatory diagram for explaining detection of endoscope insertion.

FIG. 9 is an explanatory diagram for explaining inflow detection of an inflow object 8.

FIG. 10 is an explanatory diagram for explaining detection of a swallowing reflex in a subject.

FIG. 13 is an explanatory diagram illustrating setting of a disorder level determination reference.

DETAILED DESCRIPTION OF THE PREFERRED EMBODIMENT(S)

Hereinafter, embodiments of the present invention will be described with reference to the drawings.

First Embodiment

Figure 1:
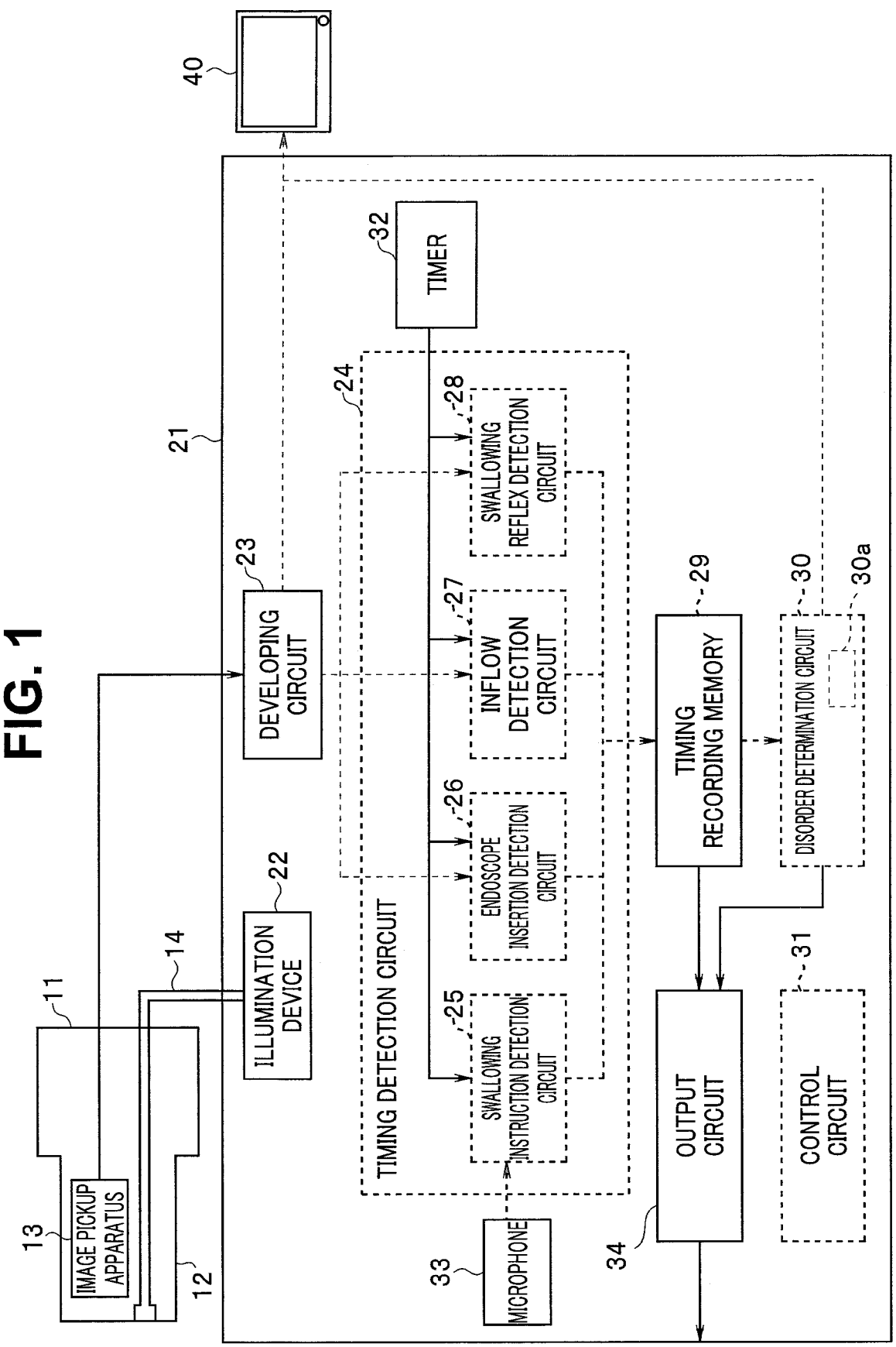
FIG. 1 is a block diagram illustrating a system for swallowing videoendoscopy according to a first embodiment of the present invention.

FIG. 1 is a block diagram illustrating a system for swallowing videoendoscopy according to a first embodiment of the present invention. In the present embodiment, based on information such as image information acquired during an examination, at least one of the following can be detected: a timing at which a doctor instructs swallowing, a timing at which an inflow object flows into the pharynx, and a swallowing reflex triggering timing in a subject. Then, based on a time relationship between the timings, diagnostic results such as a pharyngeal swallowing disorder, a swallowing reflex disorder, and an inflow object residual disorder can be obtained.

Figure 2:
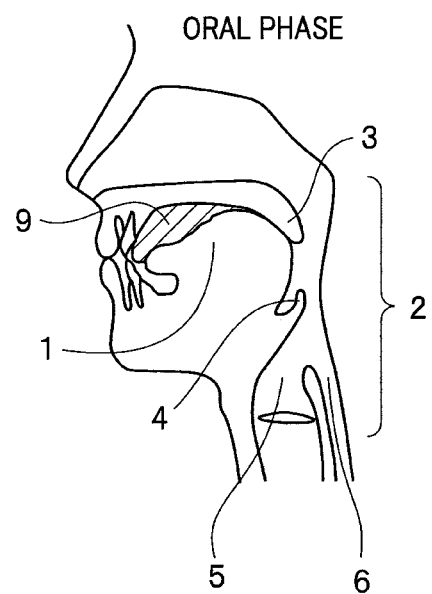
FIG. 2 is an explanatory diagram illustrating a mechanism of swallowing.
Figure 3:
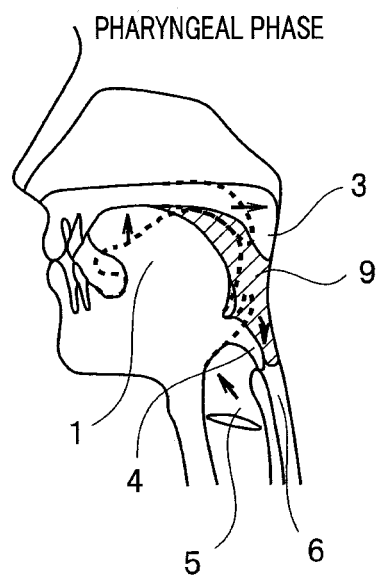
FIG. 3 is an explanatory diagram illustrating the mechanism of the swallowing.
Figure 4:
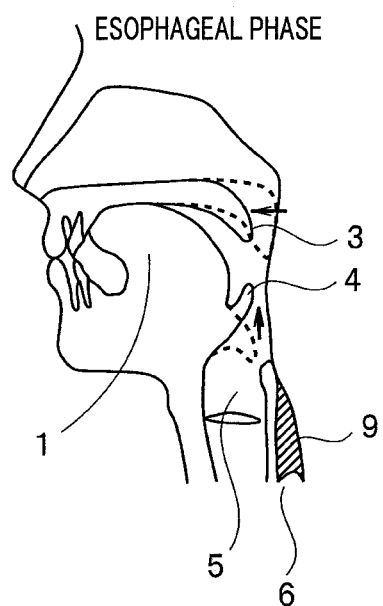
FIG. 4 is an explanatory diagram illustrating the mechanism of the swallowing.

FIGS. 2 to 7 are explanatory diagrams for explaining normal swallowing actions. FIGS. 2 to 4 illustrate a mechanism of swallowing. FIG. 2 illustrates an oral phase, FIG. 3 illustrates a pharyngeal phase, and FIG. 4 illustrates an esophageal phase.

FIG. 2 illustrates the oral phase in which a bolus 9 (hatched area) is held in the oral cavity. The tongue 1 rises upward and the soft palate 3 lowers downward to separate the oral cavity from the pharynx 2 and hold the bolus 9 in the mouth so that the bolus 9 can be chewed and swallowed as necessary. In this state, the bolus 9 does not flow into the esophagus 6, and the epiglottis 4 is raised to open the airway 5.

When chewing is completed, a movement of the tongue 1 and contraction of the pharynx 2 feed the bolus 9 from the oral cavity into the esophagus 6. FIG. 3 illustrates the pharyngeal phase. Broken lines in FIG. 3 illustrate states of the tongue 1, the soft palate 3, and the epiglottis 4 during the oral phase. During the pharyngeal phase, the tongue 1, the soft palate 3, and the epiglottis 4 change as indicated by arrows, whereby the bolus 9 is fed into the esophagus 6. In the case above, the epiglottis 4 is lowered (closed) to occlude the airway 5 and prevent the bolus 9 from entering the airway 5.

FIG. 4 illustrates the esophageal phase in which the bolus 9 flows into the esophagus 6. When the bolus 9 flows into the esophagus 6, the epiglottis 4 rises and returns to an original position thereof (opens), thereby connecting the airway 5 to the oral cavity and the nasal cavity, and allowing breathing. Broken lines in FIG. 4 illustrate states of the soft palate 3 and the epiglottis 4 during the pharyngeal phase. During the esophageal phase, the soft palate 3 and the epiglottis 4 change as indicated by arrows, thereby opening the airway 5. Dysphagia is an abnormality that occurs in any of the swallowing actions illustrated in FIGS. 2 to 4.

Figure 5:
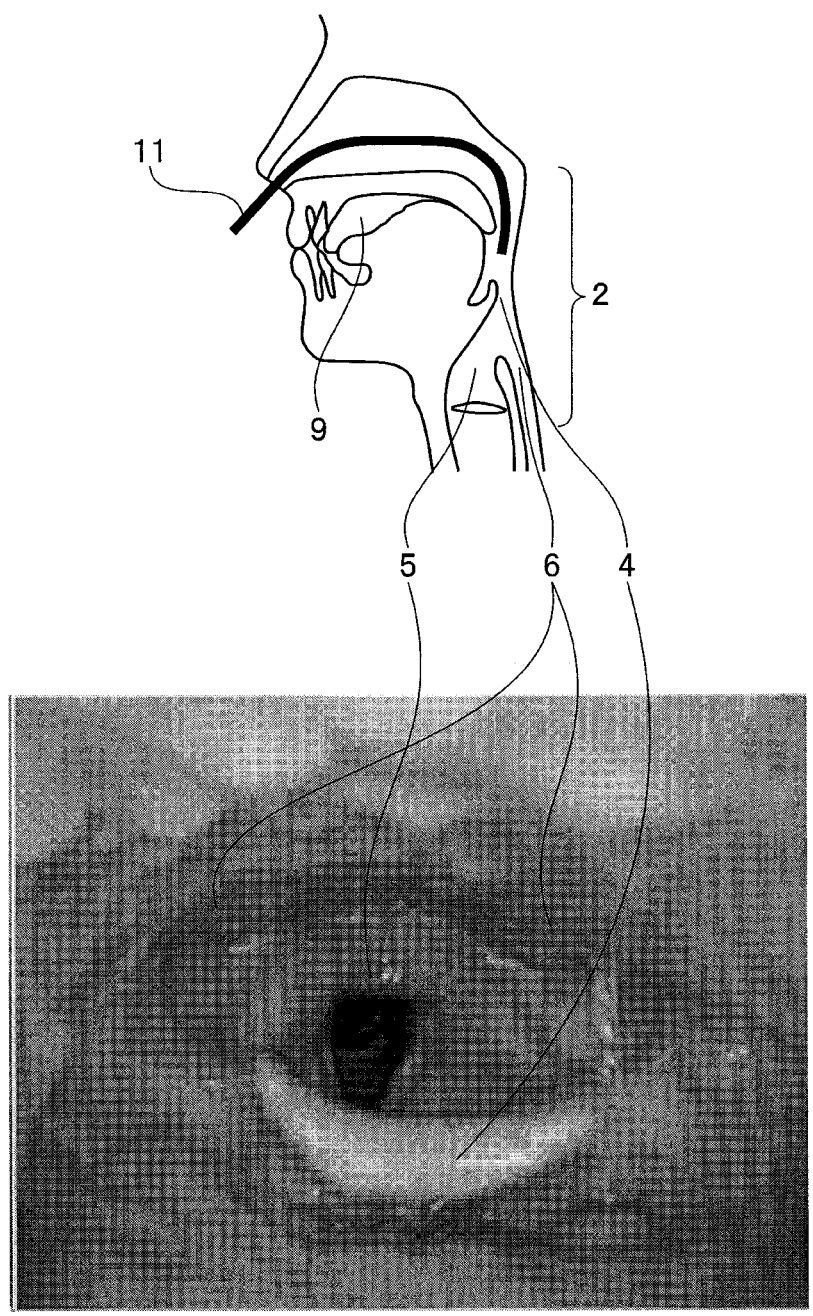
FIG. 5 is an explanatory diagram for explaining a general method for confirming a swallowing action in swallowing videoendoscopy.

FIG. 5 is an explanatory diagram for explaining a typical method for confirming the swallowing action in swallowing videoendoscopy. The upper part of FIG. 5 illustrates an endoscope 11 inserted into the nasal cavity for the swallowing videoendoscopy.

As will be described later, the endoscope 11 is provided with an image pickup apparatus (not illustrated) at a distal end of an elongated and flexible insertion portion. During the examination, a distal end portion of the endoscope 11 is stopped at an upper end of the pharynx 2 and positioned so that an optical axis of an image pickup device at the distal end faces the esophagus 6 side. With the endoscope 11, it is possible to observe the pharynx 2, the esophagus 6, the food for examination flowing from the pharynx 2 to the esophagus 6, the airway 5, a movement of the epiglottis 4 that occludes the airway 5, and the like.

The lower part of FIG. 5 illustrates an image acquired by the endoscope 11. In the example in FIG. 5, the picked-up image shows an opening of the airway 5 in the center of the image, the epiglottis 4 in an open state below the airway 5, and the esophagus 6 in an occluded state above and to the left and right of the airway 5. That is, FIG. 5 illustrates an image before the bolus 9 flows into the pharynx 2.

By using the endoscope 11 to acquire images in the oral phase, the pharyngeal phase, and the esophageal phase and observing states of swallowing from the acquired images, an operator can diagnose dysphagia. In the present embodiment, by detecting various kinds of timings using information such as image information, thereby enabling effective diagnostic support for dysphagia.

Figure 6:
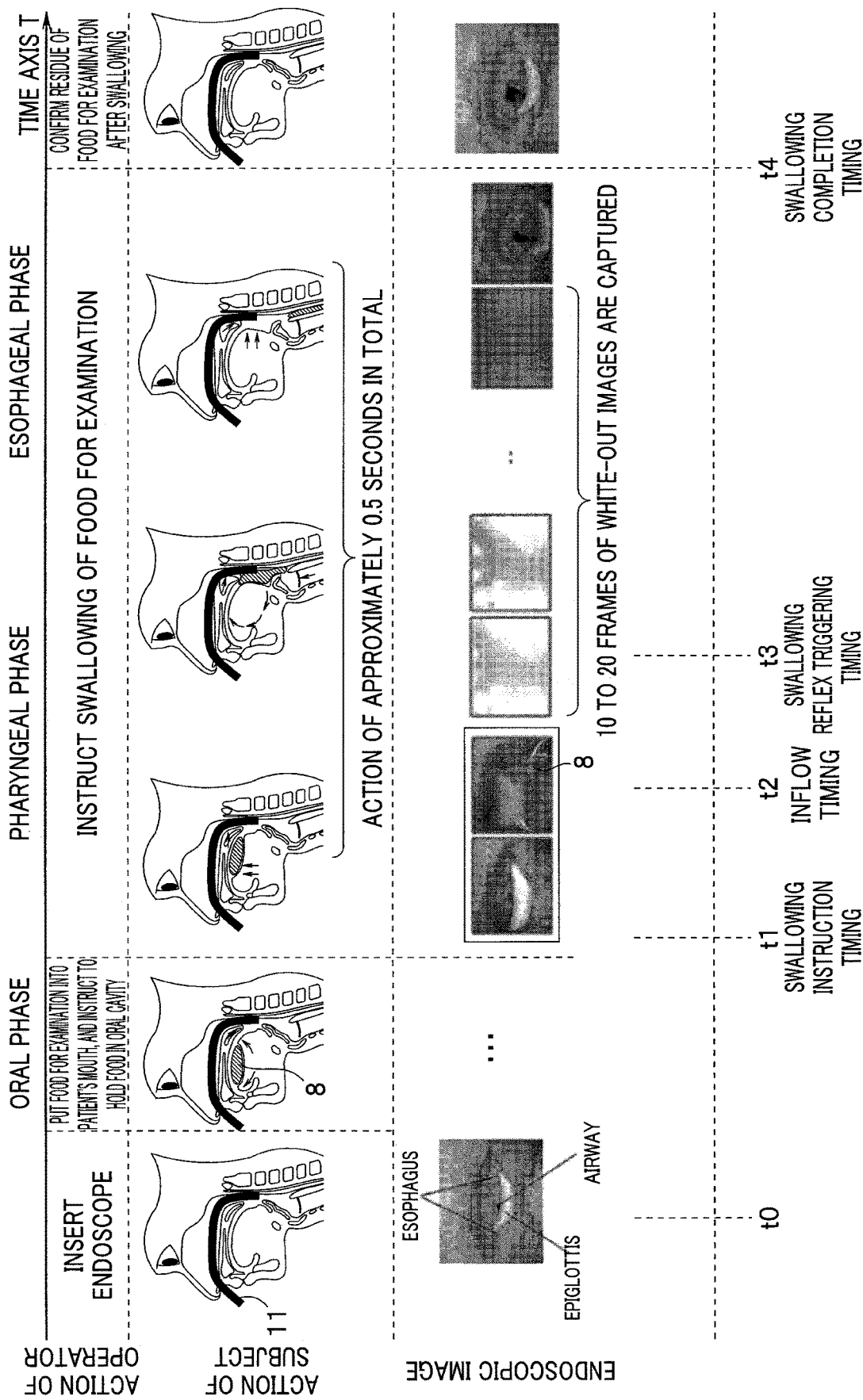
FIG. 6 is an explanatory diagram for explaining the swallowing videoendoscopy.
Figure 7:
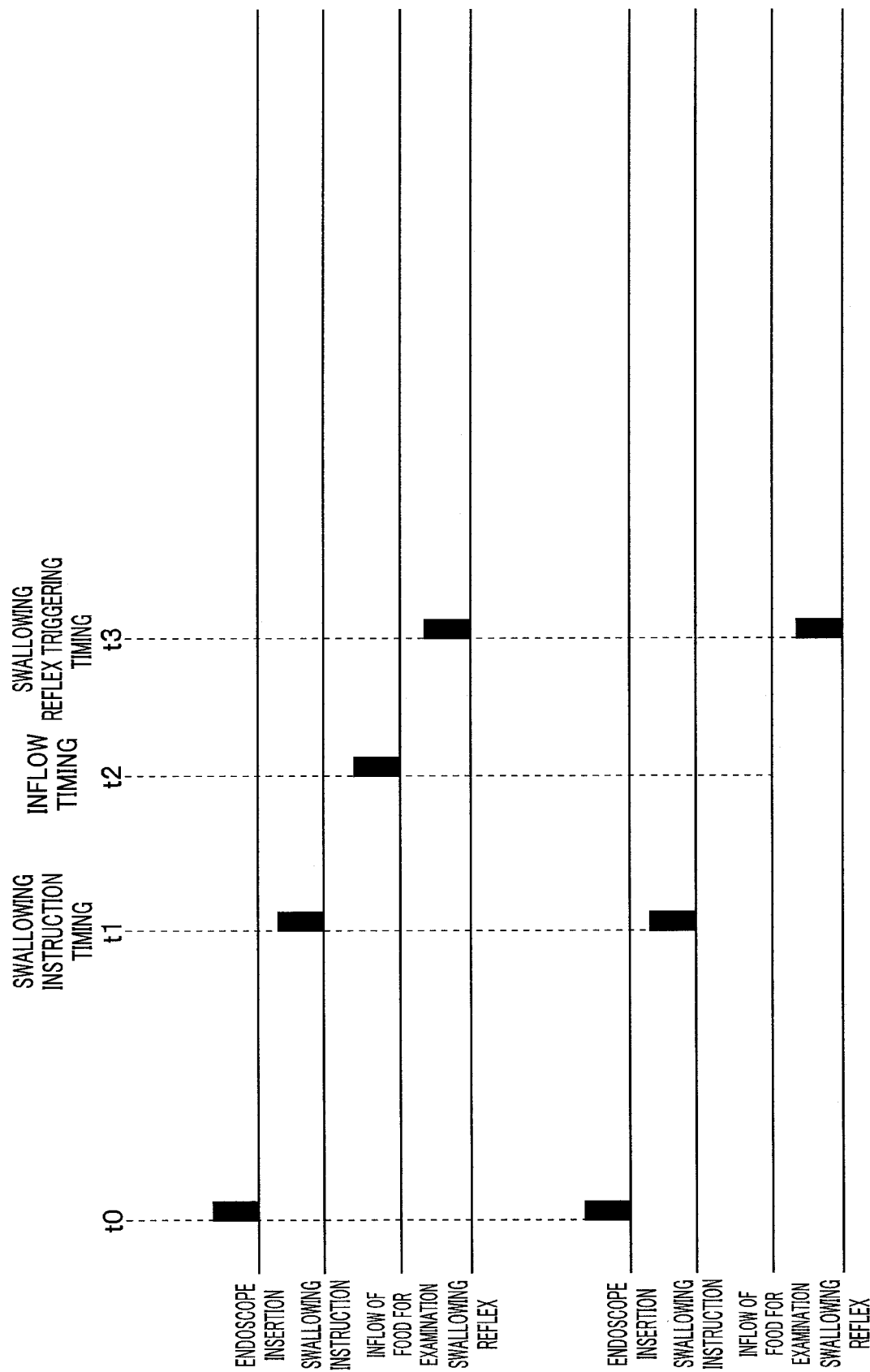
FIG. 7 is an explanatory diagram for explaining a normal swallowing action.

FIG. 6 is an explanatory diagram illustrating the swallowing videoendoscopy, specifically, changes in the actions of an operator and a subject (operator actions and subject actions) during the normal swallowing action and endoscopic images acquired at corresponding times, with time on the horizontal axis. FIG. 7 is an explanatory diagram illustrating a timing at which the doctor instructs swallowing (hereinafter referred to as "swallowing instruction timing"), a timing at which the inflow object flows into the pharynx (hereinafter referred to as "inflow timing"), and a triggering timing of a swallowing reflex in the subject (hereinafter referred to as "swallowing reflex triggering timing") during the normal swallowing action, with a time axis that matches the time axis of FIG. 6.

A timing t0 in FIG. 6 illustrates a state in which the distal end portion of the inserted endoscope 11, which is indicated by a thick line, is stopped at a position at which the pharynx 2 can be observed at the upper end of the pharynx 2 (hereinafter referred to as "examination position"). When the examination is started, the operator puts an inflow object 8 (food for examination in FIG. 6) indicated by hatched lines into the subject's mouth, and instructs the subject to hold the inflow object 8 in the oral cavity. In FIG. 6, a column of the subject action in the oral phase illustrates the subject holding the inflow object 8 in the oral cavity. In this state, as illustrated in the endoscopic image in FIG. 6, the airway 5, the esophagus 6, and the epiglottis 4 that does not cover the airway 5 are observed.

A timing t1 in FIG. 6 indicates a swallowing instruction timing at which the operator instructs the swallowing of the inflow object 8. When the operator gives a swallowing instruction at the swallowing instruction timing t1, the subject swallows the inflow object 8 into the esophagus 6 by a series of actions of the tongue 1, the pharynx 2, the soft palate 3, and the epiglottis 4 as described above. In FIG. 6, a column of the subject action in the pharyngeal phase and the esophageal phase illustrates the actions of the subject moving the inflow object 8 from the oral cavity to the pharynx 2 and then flows the inflow object 8 into the esophagus 6.

According to the series of swallowing actions of the subject, the images picked up by the endoscope 11 vary as illustrated in FIG. 6. The normal swallowing action is performed in a very short time of approximately 0.5 seconds in total, so accurate diagnosis may be difficult for an unskilled person. In the present embodiment, in order to enable a quantitative diagnosis of dysphagia based on more objective facts, the series of swallowing actions swallowing an inflow object such as food for examination from the mouth into the esophagus 6 is determined at three timings. That is, in addition to the swallowing instruction timing t1, a timing at which the inflow object flows into the pharynx 2 is defined as an inflow timing t2, and a timing at which the epiglottis 4 closes to occlude the airway 5 and the esophagus 6 opens (swallowing reflex is triggered) is defined as a swallowing reflex triggering timing t3.

As illustrated in FIG. 6, at the inflow timing t2, the inflow object 8 (hatched portion) appears in the pharynx 2 in the endoscopic image. At the swallowing reflex triggering timing t3, due to the contraction of the pharynx 2 and the action of the epiglottis 4, the living tissue approaches or comes into close contact with the distal end portion of the endoscope 11, resulting in a white-out image in which the entire endoscopic image is white, as will be described later. The endoscope acquires approximately 10 to 20 frames of white-out images, and then again acquires images showing a contour of the pharynx 2.

A timing t4 in FIG. 6 is a swallowing completion timing at which the swallowing reflex ends and movement of the inflow object into the esophagus 6 is completed. After the swallowing completion timing t4, the operator can confirm the inflow object residual disorder by checking whether the inflow object 8 remains in the pharynx 2. In FIG. 6, the column of the subject action indicates that the swallowing action is completed after the swallowing completion timing t4. In the endoscopic image after the swallowing completion timing t4, the inflow object 8 does not remain in the epiglottis 4, the airway 5, and the esophagus 6.

FIG. 7 shows timing charts for two examples in which the swallowing action is normal, in order to outline a method for determining dysphagia according to the present embodiment. In the present embodiment, the pharyngeal swallowing disorder, the swallowing reflex disorder, and the inflow object residual disorder can be determined based on the swallowing instruction timing t1, the inflow timing t2, and the swallowing reflex triggering timing t3.

Timings indicated by solid rectangles in FIG. 7 indicate the timings of the insertion of the endoscope 11, the instruction for swallowing, the inflow of the inflow object 8, and the triggering of the swallowing reflex, respectively. As described with reference to FIG. 6, the timing t0 in FIG. 7 is the timing at which the examination is started and the subject holds the inflow object 8 in the oral cavity. At the swallowing instruction timing t1, the operator instructs the subject to swallow the inflow object 8.

The pharyngeal swallowing disorder is a disorder in which the subject cannot normally hold the inflow object 8 in the oral cavity. A disorder in which the inflow object 8 cannot be held in the oral cavity and flows into the pharynx too early is referred to as "premature spillage into the pharynx", whereas a disorder in which the inflow object 8 flows into the pharynx is too late is referred to as "delayed pharyngeal swallow". Both disorders are the pharyngeal swallowing disorders due to muscle weakness of the tongue 1 or the like.

In FIG. 7, by comparing a period from the swallowing instruction timing t1 to the inflow timing t2 with a predetermined threshold value, the pharyngeal swallowing disorder can be determined.

The swallowing reflex disorder is a disorder in which the swallowing reflex is not triggered at an appropriate timing. A disorder in which the swallowing reflex occurs later than an appropriate timing is referred to as "delayed swallowing reflex", whereas a disorder in which the swallowing reflex occurs earlier than the appropriate timing is referred to as "premature swallowing reflex". The swallowing reflex is an involuntary reflex, and the swallowing reflex disorder occurs due to decreased sensation or the like.

In the upper part of FIG. 7, by comparing a period from the inflow timing t2 to the swallowing reflex triggering timing t3 with a predetermined threshold value, the swallowing reflex disorder can be determined.

The inflow object residual disorder is a disorder in which food or drink remains in the pharynx or trachea upon completion of swallowing (inflow object residue), and is caused by a weakening of the ability to close the throat and swallow.

Even when the swallowing action is normal, the inflow timing t2 and the swallowing reflex triggering timing t3 may be very close to each other, or the swallowing reflex triggering timing t3 may precede the inflow timing t2. In the case above, the inflow of the inflow object 8 into the pharynx 2 at the inflow timing t2 may not be confirmed by observation using the picked-up image due to the white-out images at the swallowing reflex triggering timing t3.

FIG. 7 illustrates an example of the case, in which the inflow timing t2 is not detected. Even in the case above, by comparing a period from the swallowing instruction timing t1 to the swallowing reflex triggering timing t3 with a predetermined threshold value, the swallowing reflex disorder can be determined, and the pharyngeal swallowing disorder can also be estimated.

(Configuration)

As illustrated in FIG. 1, a system for the swallowing videoendoscopy mainly includes the endoscope 11, a main circuit 21, and a monitor 40. The endoscope 11 is connected to the main circuit 21 by a cable (not illustrated) or wirelessly. The endoscope 11 includes an insertion portion 12 on a distal end side and an operation portion on a proximal end side. An image pickup apparatus 13 having an image pickup device such as a CCD or CMOS sensor is disposed at the distal end portion of the insertion portion 12. A light guide 14 for transmitting illumination light for illuminating an object is disposed in the insertion portion 12, and the illumination light transmitted through the light guide 14 is applied to the object via a lens (not illustrated) at the distal end of the insertion portion 12.

Return light from the object is picked up on an image pickup surface of the image pickup apparatus 13 via an observation lens (not illustrated) at the distal end of the insertion portion 12. The image pickup apparatus 13 obtains a picked-up image based on an optical image of the object by photoelectric conversion. The picked-up image from the image pickup apparatus 13 is supplied to the main circuit 21 via signal lines and cables disposed in the insertion portion 12 and the operation portion.

The main circuit 21 includes a control circuit 31. The control circuit 31 can control individual units in the main circuit 21, and the endoscope 11. For example, the control circuit 31 may be configured by a processor using a central processing unit (CPU), a field programmable gate array (FPGA), or the like, may operate in accordance with a program stored in a memory (not illustrated) to control individual units, or may implement some or all of the functions by electronic circuits of hardware.

The control circuit 31 supplies clocks and various drive signals to the image pickup apparatus 13 of the endoscope 11 to drive the image pickup apparatus 13. The main circuit 21 includes an illumination device 22 that supplies illumination light to the endoscope 11 and a developing circuit 23 that develops an image pickup signal from the image pickup apparatus 13 and outputs a video signal of an endoscopic image. The illumination device 22 includes a light source such as an LED, and generates illumination light. The illumination light is guided to the distal end portion of the endoscope 11 by the light guide 14 and is applied onto the object. Alternatively, the illumination device 22 and the light guide 14 may be omitted, and the object may be illuminated by an illumination device built into the endoscope 11.

The developing circuit 23 obtains a video signal by developing the picked-up image from the image pickup apparatus 13. For example, a so-called RAW image is inputted as a picked-up image from the image pickup apparatus 13. The developing circuit 23 processes the RAW image for image display or the like based on the RAW image, based on various kinds of information such as information on the image size of the image pickup device of the image pickup apparatus 13, information indicating whether an image pickup method is a frame sequential method or a simultaneous method, and information on the observation mode specified by the control circuit 31.

The picked-up image (endoscopic image) processed by the developing circuit 23 is supplied to the monitor 40. The monitor 40 displays the inputted endoscopic image. Thus, the picked-up image during the examination can be observed on the display screen of the monitor 40.

(Timing Detection)

Further, the endoscopic image from the developing circuit 23 is also supplied to a timing detection circuit 24. The timing detection circuit 24 includes a swallowing instruction detection circuit 25, an endoscope insertion detection circuit 26, an inflow detection circuit 27, and a swallowing reflex detection circuit 28. At least one circuit in the timing detection circuit 24 and a disorder determination circuit 30 to be described later may be configured by a processor using a CPU, an FPGA, or the like, may operate in accordance with a program stored in a memory (not illustrated) to control individual units, or may implement some or all of functions by electronic circuits of hardware.

The timing detection circuit 24 is also supplied with an output of a timer 32. The timer 32 generates information about the current time or the time from the activation of the main circuit 21 or the image pickup apparatus 13 and outputs the information to individual circuits in the timing detection circuit 24. The main circuit 21 may be provided with a microphone 33. The microphone 33 collects ambient sound and outputs the sound to the individual circuits in the timing detection circuit 24. For example, the microphone 33 may be used to capture the voice of the operator instructing swallowing and supply the captured voice to the swallowing instruction detection circuit 25. Note that an input operation section such as a button (not illustrated) may be provided in the main circuit 21 or the endoscope 11, which is operated to notify the timing detection circuit 24 of the swallowing instruction by the operator or the like.

The swallowing instruction detection circuit 25 detects the timing of the swallowing instruction by the operator based on an audio signal from the microphone 33 or the operation signal from the input operation section (not illustrated). For example, the swallowing instruction detection circuit 25 may detect the timing of the swallowing instruction by the operator by audio recognition processing on the inputted audio signal, or may detect the timing of the swallowing instruction by the operator by detecting an input of a predetermined audio waveform.

The swallowing instruction detection circuit 25 outputs a detection result of the swallowing instruction timing to a timing recording memory 29 together with time information from the timer 32. The timing recording memory 29 is constituted of a predetermined recording medium and records various kinds of timing information (time information) detected by the individual circuits in the timing detection circuit 24.

The endoscope insertion detection circuit 26 detects that the endoscope 11 has been inserted into the nasal cavity and the distal end portion thereof has reached the examination position, and records the detection timing of insertion (hereinafter referred to as "insertion detection timing") in the timing recording memory 29 using the time information from the timer 32. For example, the endoscope insertion detection circuit 26 may perform image analysis on the picked-up image from the developing circuit 23 and detect the insertion of the endoscope 11 based on the analysis result.

FIG. 8 is an explanatory diagram for explaining the detection of the endoscope insertion. FIG. 8 illustrates images picked up by the image pickup apparatus 13. Images P1 and P2 are images before the distal end portion of the endoscope 11 reaches the examination position, and an image P3 is an image after the distal end portion of the endoscope 11 reaches the examination position. Note that the image P1 is an image obtained when the distal end portion of the endoscope 11 is wiped with a cloth or the like before insertion of the endoscope 11. The image P3 is obtained by picking up an image of part of the pharynx 2 at the examination position, and typically is an image having many red components. On the other hand, the images P1 and P2 have fewer red components.

The endoscope insertion detection circuit 26 can detect that the endoscope 11 has been inserted into the nasal cavity and the distal end portion thereof has reached the examination position, for example, by determining the color of the picked-up image. For example, the endoscope insertion detection circuit 26 may detect that the distal end portion of the endoscope 11 has reached the examination position by comparing the number of pixels within a predetermined color space that includes a red hue in the image to a threshold value. After the endoscope insertion detection circuit 26 detects that the distal end portion of the endoscope 11 has reached the examination position, the endoscope insertion detection circuit 26 may record the timing of the detection in the timing recording memory 29 as the insertion detection timing.

The endoscope insertion detection circuit 26 may acquire the insertion detection timing based on an audio signal from the microphone 33 that collects the operator's speech or an operation signal from the input operation section (not illustrated).

The inflow detection circuit 27 detects that the inflow object 8 in the oral cavity of the subject has flowed into the pharynx 2, and records the timing of the detection (inflow timing) in the timing recording memory 29. For example, the inflow detection circuit 27 may perform image analysis on the picked-up image from the developing circuit 23 and may detect the inflow of the inflow object 8 based on the analysis result.

FIG. 9 is an explanatory diagram for explaining the inflow detection of the inflow object 8. FIG. 9 illustrates images picked up by the image pickup apparatus 13. An image P5 is an image before the inflow object 8 flows into the pharynx 2, and an image P6 is an image when the inflow object 8 has flowed into the pharynx 2. The image P5 and the image P6 are substantially the same images except for the presence or absence of a portion (hatched portion) corresponding to the inflow object 8 in the image. The image P5 as a whole has substantially the color of living tissue, that is, a reddish color. On the other hand, the image P6 has a color influenced by the color of the inflow object 8 in a portion into which the inflow object 8 has flowed.

FIG. 9 illustrates an example in which the inflow object 8 is purple. For example, it is assumed that the (R, G, B) value of the average hue of a region P5a of the image P5 is (161, 102, 79) in the RGB color system, and the (R, G, B) value of the average hue of a region P6a of the image P6 at the same position as the region P5a is (152, 73, 118) in the RGB color system. That is, in the case above, while the average color of the region P5a is close to the red color of the living tissue, the average color of the region P6a is close to the purple color of the inflow object 8. Therefore, the region P6a is considered to correspond to the portion into which the inflow object 8 has flowed. For example, the inflow detection circuit 27 may detect the inflow of the inflow object 8 according to whether an area of an image region having the color similar to the color of the inflow object 8 is larger than a threshold value.

Note that the color of the inflow object 8 is not limited to purple, and can be any color such as blue or white that can be easily distinguished from the color of the living tissue. Further, food or the like that meets the preference of the subject may be employed as the inflow object 8. Even in the case above, when the color of the inflow object 8 is different from the color of the living tissue, the inflow of the inflow object 8 can be detected.

Even before the endoscope 11 is inserted into the nasal cavity, the image acquired by the image pickup apparatus 13 may be an image that includes many areas having the color similar to the color of the inflow object 8. Thus, in order to distinguish between the image obtained by the inflow of the inflow object 8 and the image before the insertion of the endoscope 11, the inflow detection circuit 27 may acquire the information on the insertion detection timing detected by the endoscope insertion detection circuit 26 from the timing recording memory 29 (not illustrated) and detect the inflow of the inflow object 8 by the image acquired after the insertion detection timing.

The swallowing reflex detection circuit 28 detects that the triggering of the swallowing reflex occurs in the subject, and records the timing of the detection (swallowing reflex triggering timing) in the timing recording memory 29. For example, the swallowing reflex detection circuit 28 may perform image analysis on the picked-up image and detect the swallowing reflex based on the analysis result.

FIG. 10 is an explanatory diagram for explaining swallowing reflex detection in the subject. FIG. 10 illustrates images picked up by the image pickup apparatus 13. An image P7 is an image before the triggering of the swallowing reflex occurs in the subject, and an image P8 is an image when the triggering of the swallowing reflex has occurred in the subject. The image P7 is an image in which a distance between the image pickup apparatus 13 and the pharynx 2 is appropriate, and the pharynx 2 is illuminated with an appropriate amount of light and is in focus, and clearly shows a state of the pharynx 2 before swallowing. On the other hand, the image P8 is an image acquired when the living tissue is close to the image pickup apparatus 13 due to the swallowing reflex.

The control circuit 31 controls light adjustment of the illumination device 22 according to the brightness of the picked-up image. For example, the control circuit 31 increases the amount of illumination light when a distance from the distal end portion to the living tissue is long, and decreases the amount of illumination light when the distance from the distal end portion to the living tissue is short, thereby adjusting the brightness of the picked-up image to appropriate brightness. However, since a distance between the image pickup apparatus 13 and the living tissue becomes short in a very short time due to the swallowing reflex, the light adjustment control for reducing the amount of illumination light is not in time, and the picked-up images become white-out images. The image P8 shows the white-out image. The image P8 is clearly brighter than the image P7, thus, the swallowing reflex detection circuit 28 can determine that the white-out image has been acquired based on the average pixel value.

Alternatively, the swallowing reflex detection circuit 28 may detect that the white-out image has been acquired by filtering the inputted picked-up image. For example, the swallowing reflex detection circuit 28 may perform edge filtering on the inputted picked-up image.

Images P9 and P10 in FIG. 10 are obtained by applying edge filtering to the images P7 and P8, respectively. The image P9 has many edge portions P9a. On the other hand, the image P10 has no edge portions. When the swallowing reflex detection circuit 28 performs edge detection on the images P9 and P10 and determines that no edge portions are detected or the number of edge portions is equal to or less than a predetermined threshold number, the swallowing reflex detection circuit 28 may determine that the white-out image has been acquired, that is, the swallowing reflex has been detected.

Since the image pickup apparatus 13 acquires the white-out images due to the swallowing reflex, and then acquires normal luminance images again in a relatively short period of time, the swallowing reflex can be detected more reliably by the determination based on the edge detection by edge filtering than by the determination based on the luminance level of the white-out image.

Even before the endoscope 11 is inserted into the nasal cavity, the image acquired by the image pickup apparatus 13 may be a white-out image. Also, after the insertion detection timing, when the subject coughs or the like, the image pickup apparatus 13 and the living tissue come close to each other, and a white-out image may be acquired. Thus, in order to distinguish a white-out image due to the swallowing reflex from white-out images due to factors other than the swallowing reflex, the swallowing reflex detection circuit 28 may acquire information on the insertion detection timing detected by the endoscope insertion detection circuit 26, information on the swallowing instruction timing, information on the inflow timing, and the like from the timing recording memory 29 (not illustrated), and detect the swallowing reflex by a white-out image acquired within a predetermined time after the insertion detection timing and the swallowing instruction timing or a white-out image acquired within a predetermined time after the inflow timing.

Although an example has been described in which the swallowing reflex detection circuit 28 detects the swallowing reflex based on whether the image pickup apparatus 13 has acquired a white-out image, other methods may be employed. When a high-speed camera is adopted as the image pickup apparatus 13, the light adjustment control may also be faster and the white-out images may not be acquired. In the case above, the swallowing reflex detection circuit 28 may detect the swallowing reflex by image analysis of an image picked up by the image pickup apparatus 13, which is the high-speed camera.

Although an example in which the swallowing reflex detection circuit 28 detects the swallowing reflex by image analysis has been described, a contact sensor (not illustrated) may be provided at the distal end portion of the endoscope 11 and the swallowing reflex may be detected using the output of the contact sensor. In the case above, the swallowing reflex detection circuit 28 may detect that the swallowing reflex has been triggered by the output of the contact sensor, which is generated by the living tissue coming into contact with the contact sensor due to the swallowing reflex.

Although an example in which each circuit in the timing detection circuit 24 records the timing information in the timing recording memory 29 using the time information from the timer 32 has been described, various kinds of timing information may be obtained using frame numbers in the picked-up images from the developing circuit 23 instead of the time information from the timer 32 and the obtained information may be recorded in the timing recording memory 29.

Any of various types of recording media, such as semiconductor recording media and magnetic recording media, can be employed for the timing recording memory 29. The timing recording memory 29 records various kinds of timing information from the timing detection circuit 24 and also outputs the recorded timing information to the disorder determination circuit 30 and an output circuit 34.

The output circuit 34 is capable of outputting the various kinds of timing information from the timing recording memory 29 and determination information about dysphagia from the disorder determination circuit 30 to an external device. For example, the output circuit 34 may include a communication circuit (not illustrated) capable of communicating with the outside by wire or wirelessly. The communication circuit may be configured to enable communication such as wireless communication using a wireless LAN such as Wi-Fi (registered trademark) or Bluetooth (registered trademark), or wired communication using a LAN cable or USB cable.

Although the output circuit 34 has been described as being capable of outputting the various kinds of timing information from the timing recording memory 29, the output circuit 34 may be configured to directly transmit the various kinds of timing information from the timing detection circuit 24 to an external device.

In addition to simply outputting the inputted various kinds of timing information, the output circuit 34 may also have a function of converting the timing information into display information for presenting to the operator or the like, converting the display information into a video signal that can be displayed on the monitor 40, and outputting the video signal.

(Disorder Determination)

The disorder determination circuit 30 reads various kinds of timing information from the timing recording memory 29 and determines whether the subject has dysphagia based on the read timing information. The disorder determination circuit 30 may also be supplied with the picked-up image from the developing circuit 23 (not illustrated). The disorder determination circuit 30 may analyze the picked-up image from the developing circuit 23 and determine dysphagia using not only the timing information but also the image analysis result.

(Pharyngeal Swallowing Disorder Determination)

Figure 11:
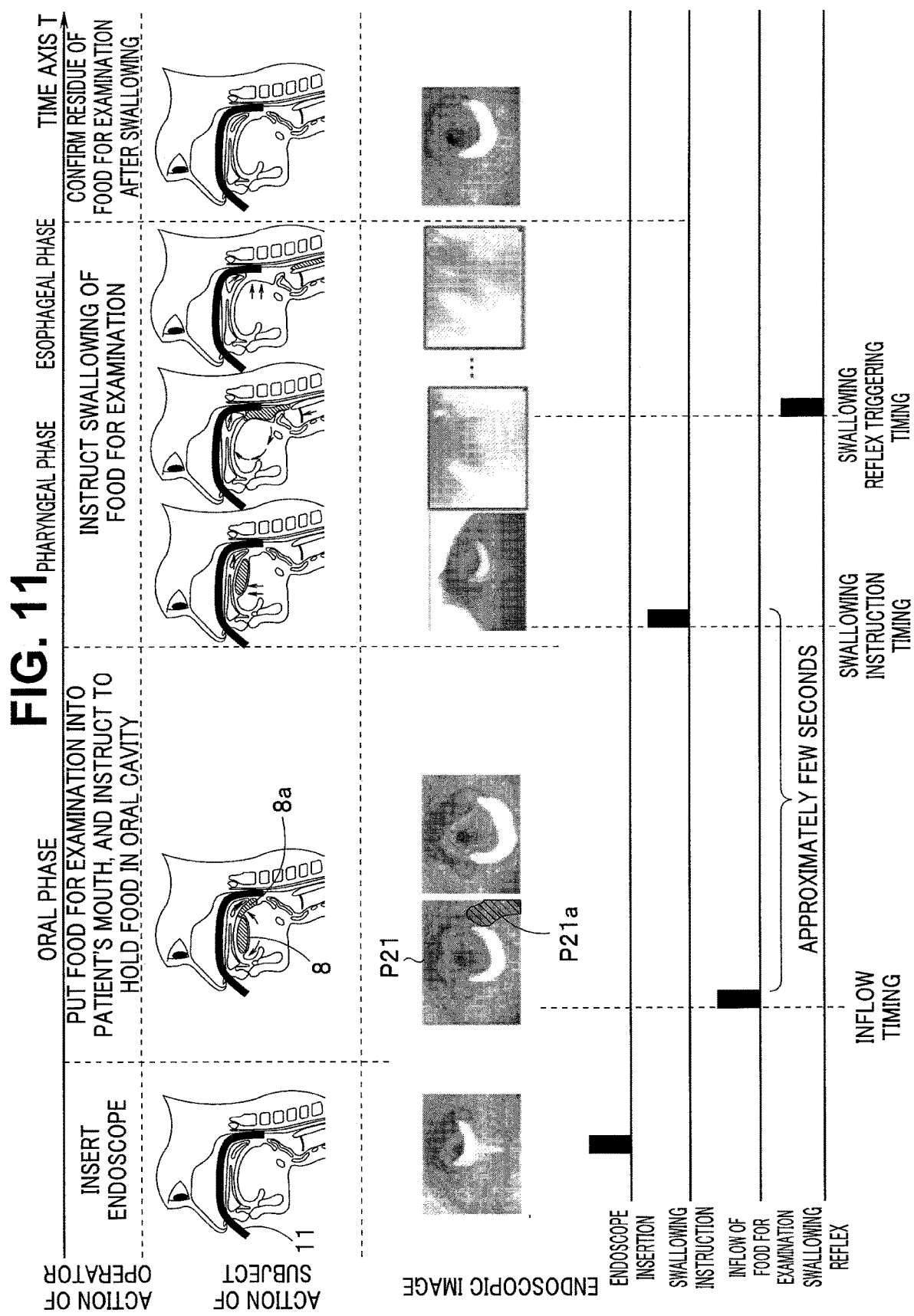
FIG. 11 is an explanatory diagram illustrating a pharyngeal swallowing disorder in a manner similar to that in FIGS. 6 and 7.
Figure 12:
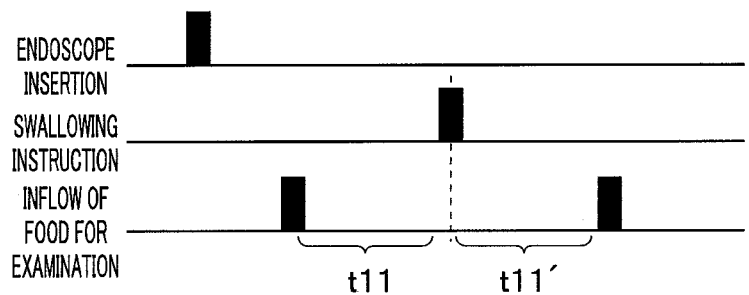
FIG. 12 is an explanatory diagram illustrating a method for determining a disorder level.
Figure 14:
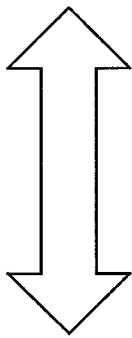
FIG. 14 is an explanatory diagram for explaining a process of determining a pharyngeal swallowing disorder in a process of determining dysphagia by a disorder determination circuit 30.

FIGS. 11 to 14 are explanatory diagrams for explaining a process of determining the pharyngeal swallowing disorder in the process of determining dysphagia by the disorder determination circuit 30. FIG. 11 illustrates a pharyngeal swallowing disorder in a manner similar to that in FIGS. 6 and 7. FIG. 12 is the diagram for explaining a method for determining a disorder level, FIG. 13 shows the setting of a disorder level determination reference, and FIG. 14 illustrates a method for determining ease of swallowing the inflow object 8.

A column of the subject action in the oral phase in FIG. 11 illustrates a state in which a part 8a of the inflow object 8 held in the oral cavity by the subject flows into the pharynx 2. The state is the premature spillage into the pharynx caused by muscle weakness of the subject or the like. The inflow detection circuit 27 can detect that the inflow object has flowed into the pharynx 2 by the color of a portion P21a (hatched portion) in a picked-up image P21 corresponding to the inflow object 8 in the case above.

When dysphagia does not occur, as illustrated in FIG. 6, the inflow object 8 flows into the pharynx 2 after the timing of the swallowing instruction by the operator. On the other hand, in the case of the premature spillage into the pharynx, as illustrated in FIG. 11, the swallowing instruction by the operator is given after the inflow timing at which the inflow object 8 flows into the pharynx 2.

When the relationship between the swallowing instruction timing and the inflow timing read from the timing recording memory 29 is opposite to the normal state, that is, when the inflow timing is earlier than the swallowing instruction timing, the disorder determination circuit 30 can determine that the subject has the premature spillage into the pharynx in the pharyngeal swallowing disorder.

Further, from the relationship between the inflow timing and the swallowing instruction timing, the disorder determination circuit 30 can determine not only the premature spillage into the pharynx but also the delayed pharyngeal swallow in the pharyngeal swallowing disorder and can also determine the disorder level of the pharyngeal swallowing disorder.

FIG. 12 illustrates the insertion detection timing (endoscope insertion), the swallowing instruction timing (swallowing instruction), and the inflow timing of the inflow object such as food for examination (inflow of food for examination) by solid rectangle positions with time on the horizontal axis. FIG. 12 illustrates a case of the premature spillage into the pharynx, in which the inflow timing is earlier than the swallowing instruction timing by a time t11, and a case of the delayed pharyngeal swallow, in which the inflow timing is later than the swallowing instruction timing by a time t11'. In a normal case, the entire swallowing action takes approximately 0.5 seconds. Thus, for example, the disorder determination circuit 30 may determine that the pharyngeal swallowing disorder is severe when t11 or t11' is approximately several tens of seconds, may determine that the pharyngeal swallowing disorder is moderate when t11 or t11' is approximately several seconds, and may determine that the pharyngeal swallowing disorder is mild when t11 or t11' is approximately one to two seconds.

The disorder determination circuit 30 includes a memory 30a that stores disorder level determination reference information that serves as a reference for determination of such a disorder level. The disorder determination circuit 30 may read the disorder level determination reference information from the memory 30a and determine the disorder level of the pharyngeal swallowing disorder by comparing information on determination reference time set in the disorder level determination reference information with a time difference between the swallowing instruction timing and the inflow timing.

FIG. 13 shows an example of the disorder level determination reference information. The example in FIG. 13 includes the information on the determination reference time for determining severe, moderate, and mild for each of the pharyngeal swallowing disorder, the swallowing reflex disorder, and the inflow object residual disorder. In the example in FIG. 13, the determination reference time varies depending on the type of inflow object such as food for examination. Some inflow objects are prone to the premature spillage into the pharynx or the delayed pharyngeal swallow. Therefore, in order to more accurately determine the pharyngeal swallowing disorder, the determination reference time differs depending on the type of inflow object.

FIG. 14 illustrates a relationship between the type of inflow object and the ease of swallowing for determining the determination reference time. The left side of FIG. 14 illustrates easy-to-swallow inflow objects, such as thickened water and jelly, which have the properties of being homogeneous, not breaking apart in the mouth, and not sticking to mucous membranes. The right side of FIG. 14 illustrates difficult-to-swallow inflow objects, such as rice gruel and general food, which have the properties of being inhomogeneous, tending to break apart in the mouth, and tending to stick to mucous membranes. In the example shown in FIG. 13, the determination reference times are set by classifying the inflow objects into two types depending on whether the inflow objects are easy to swallow, but the inflow objects may be classified into three or more types.

In the example in FIG. 13, the determination reference time for the severe disorder is longer than the determination reference time for the moderate disorder, the determination reference time for the moderate disorder is longer than the determination reference time for the mild disorder, and these determination reference times have durations. In the example in FIG. 13, the determination reference times of approximately several tens of seconds, approximately several seconds, and approximately 1 to 2 seconds correspond to, for example, a time longer than 20 seconds, a time longer than 2 seconds and shorter than or equal to 20 seconds, and a time of 1 to 2 seconds, respectively. In the following description, the setting example above is referred to as a first setting of the determination reference time.

For example, assuming that the swallowing videoendoscopy is performed using an inflow object that is easy to swallow in the first setting of the determination reference time, when the t11 or t11' in FIG. 12 is 1.5 seconds, the disorder determination circuit 30 determines that the subject has a mild pharyngeal swallowing disorder, when the t11 or t11' is 5 seconds, the disorder determination circuit 30 determines that the subject has a moderate pharyngeal swallowing disorder, and when the t11 or t11' is 25 seconds, the disorder determination circuit 30 determines that the subject has a severe pharyngeal swallowing disorder. When the t11 or t11' in FIG. 12 is 0.5 seconds, the disorder determination circuit 30 determines that the pharyngeal swallowing disorder has not occurred because the pharyngeal swallowing is within the normal range. That is, when the time t11 is shorter than the determination reference time for the mild disorder, the subject may be determined to be normal even when the inflow timing is earlier than the swallowing instruction timing.

The disorder determination circuit 30 is capable of updating the disorder level determination reference information recorded in the memory 30a. For example, the operator or the like can give an instruction to the disorder determination circuit 30 using an input device (not illustrated) to update the information on the determination reference time and the information on the type of the inflow object in the disorder level determination reference information. Alternatively, the disorder determination circuit 30 may receive the disorder level determination reference information from an external device via a communication circuit (not illustrated).

The disorder level determination reference information in FIG. 13 is applicable not only to the pharyngeal swallowing disorder but also to other types of dysphagia. Although the example in FIG. 13 shows an example of setting a common determination reference time for all of the pharyngeal swallowing disorder, the swallowing reflex disorder, and the inflow object residual disorder, it is apparent that different determination reference times may be set for the different types of dysphagia. Although FIG. 13 shows an example in which the determination reference time varies depending on the type of the inflow object, the determination reference time may vary depending on the age of the subject. Thus, the determination reference time can be set according to various factors.

(Swallowing Reflex Disorder Determination)

Figure 15:
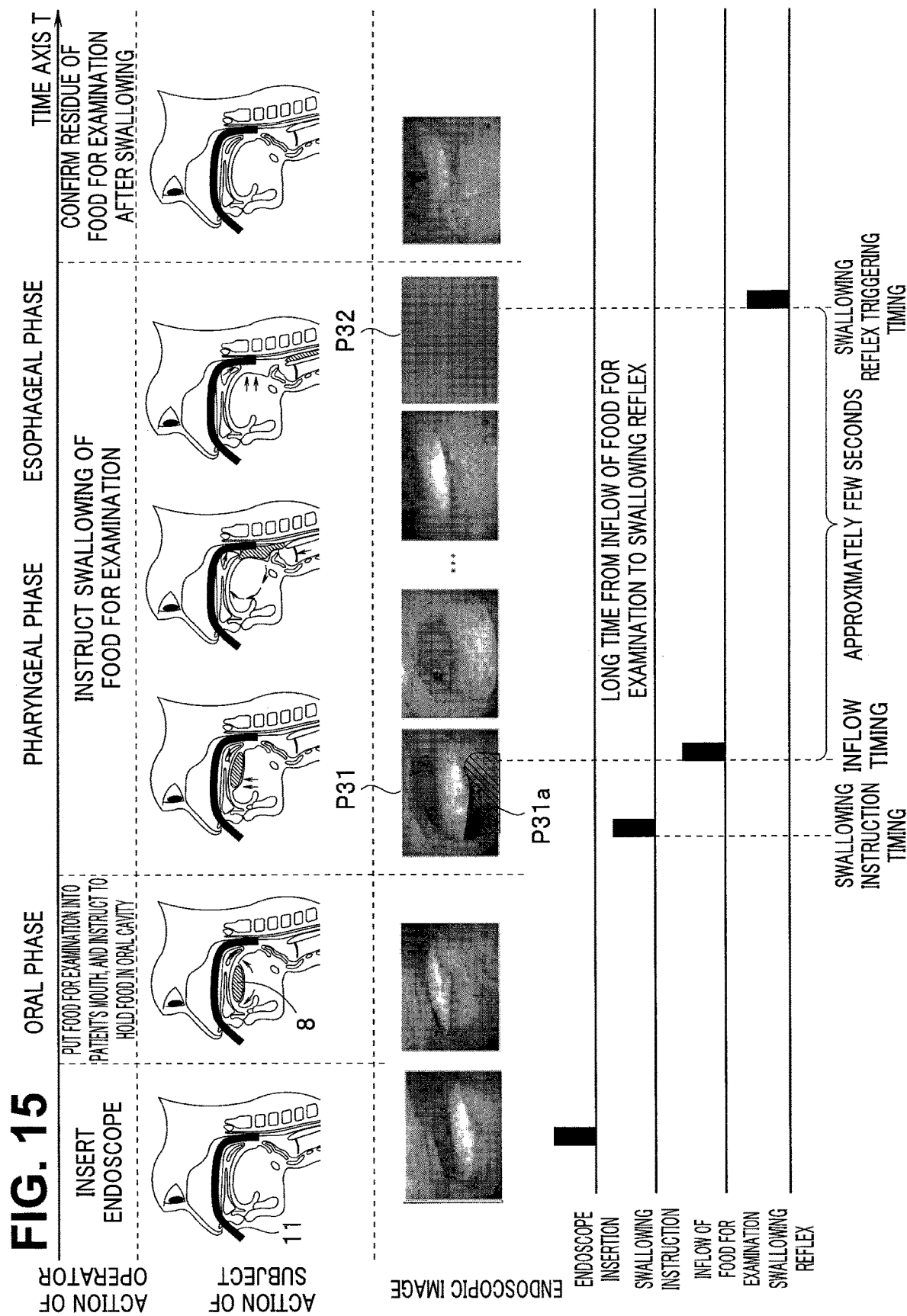
FIG. 15 is an explanatory diagram illustrating a swallowing reflex disorder in the manner similar to that in FIGS. 6 and 7.
Figure 16:
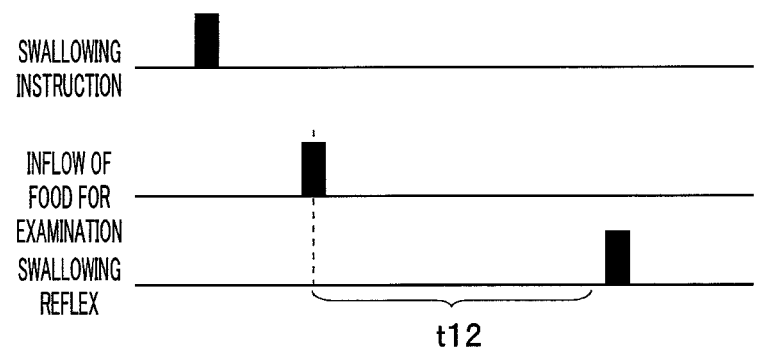
FIG. 16 is an explanatory diagram for explaining a process of determining a swallowing reflex disorder in the process of determining dysphagia by the disorder determination circuit 30.

FIGS. 15 and 16 are explanatory diagrams for explaining a process of determining the swallowing reflex disorder in the process of determining dysphagia by the disorder determination circuit 30. FIG. 15 illustrates the swallowing reflex disorder in the manner similar to that in FIGS. 6 and 7. FIG. 16 is the diagram for explaining a method for determining the disorder level.

A column of the subject action in the pharyngeal phase in FIG. 16 illustrates a process in which the subject flows the inflow object 8 held in the oral cavity from the pharynx 2 to the esophagus 6. In the example in FIG. 16, the time from the inflow of the inflow object 8 into the pharynx 2 to the triggering of the swallowing reflex is relatively long. The above is the delayed swallowing reflex caused by, for example, decreased sensation of the subject or the like. The swallowing reflex disorder can be determined by the time from the inflow timing when the inflow object 8 flows into the pharynx 2 to the swallowing reflex triggering timing or the time from the swallowing instruction timing when the operator instructs swallowing to the swallowing reflex triggering timing.

The swallowing instruction detection circuit 25 detects the swallowing instruction timing by the voice of the operator instructing swallowing or the operation of the swallowing instruction to the input operation section. The inflow detection circuit 27 detects the inflow timing based on the color of a portion P31a (hatched portion) in a picked-up image P31 corresponding to the inflow object 8. The swallowing reflex detection circuit 28 detects the swallowing reflex triggering timing by determining that an image P32 picked up by the image pickup apparatus 13 is a white-out image.

When dysphagia does not occur, as illustrated in FIG. 6, the swallowing reflex is triggered in a relatively short time from the timing of the swallowing instruction by the operator or the inflow timing of the inflow object 8. On the other hand, in the delayed swallowing reflex, as illustrated in FIG. 16, the swallowing reflex is triggered a relatively long time after the swallowing instruction timing and the inflow timing.

When a time difference between the swallowing instruction timing or the inflow timing read from the timing recording memory 29 and the swallowing reflex triggering timing is longer than the determination reference time, the disorder determination circuit 30 can determine that the subject has the delayed swallowing reflex in the swallowing reflex disorder.

FIG. 16 illustrates the swallowing instruction timing, the inflow timing, and the swallowing reflex triggering timing by solid rectangle positions with time on the horizontal axis. FIG. 16 illustrates a case of the delayed swallowing reflex, in which the swallowing reflex triggering timing is delayed by a time t12 relative to the inflow timing.

The disorder determination circuit 30 may read the disorder level determination reference information from the memory 30a and determine the disorder level of the swallowing reflex disorder by comparing the information on the determination reference time set in the disorder level determination reference information with the time difference between the swallowing instruction timing or the inflow timing and the swallowing reflex triggering timing.

In FIG. 13, for example, assuming that the swallowing videoendoscopy is performed using an inflow object that is easy to swallow in the first setting of the determination reference time, when the t12 in FIG. 16 is 1.5 seconds, the disorder determination circuit 30 determines that the subject has a mild swallowing reflex disorder, when the t12 is 5 seconds, the disorder determination circuit 30 determines that the subject has a moderate swallowing reflex disorder, and when the t12 is 25 seconds, the disorder determination circuit 30 determines that the subject has a severe swallowing reflex disorder. When the t12 in FIG. 16 is 0.5 seconds, the disorder determination circuit 30 determines that the swallowing reflex disorder has not occurred because the swallowing reflex triggering is within a normal range.

In the example illustrated in FIG. 16, an example is described in which the determination is made based on the time difference between the inflow timing and the swallowing reflex triggering timing on the assumption that the inflow timing has been detected. However, when the inflow timing is not detected, the determination may be made based on the time difference between the swallowing instruction timing and the swallowing reflex triggering timing.

From the time difference between the swallowing instruction timing or the inflow timing and the swallowing reflex triggering timing, the disorder determination circuit 30 can determine not only the delayed swallowing reflex but also the premature swallowing reflex in the swallowing reflex disorder. In the case above, a range between a minimum time difference and a maximum time difference that can be determined to be normal is determined from the swallowing instruction timing or the inflow timing, and when the time difference is out of the range, the subject is determined to have the swallowing reflex disorder. When the time difference between the swallowing instruction timing or the inflow timing and the swallowing reflex triggering timing is shorter than the minimum time difference, the disorder determination circuit 30 determines the disorder level of the premature swallowing reflex according to the degree of the time difference. On the other hand, when the time difference between the swallowing instruction timing or the inflow timing and the swallowing reflex triggering timing is longer than the maximum time difference, the disorder determination circuit 30 determines the disorder level of the delayed swallowing reflex according to the degree of the time difference.

(Inflow Object Residual Disorder Determination)

Figure 17:
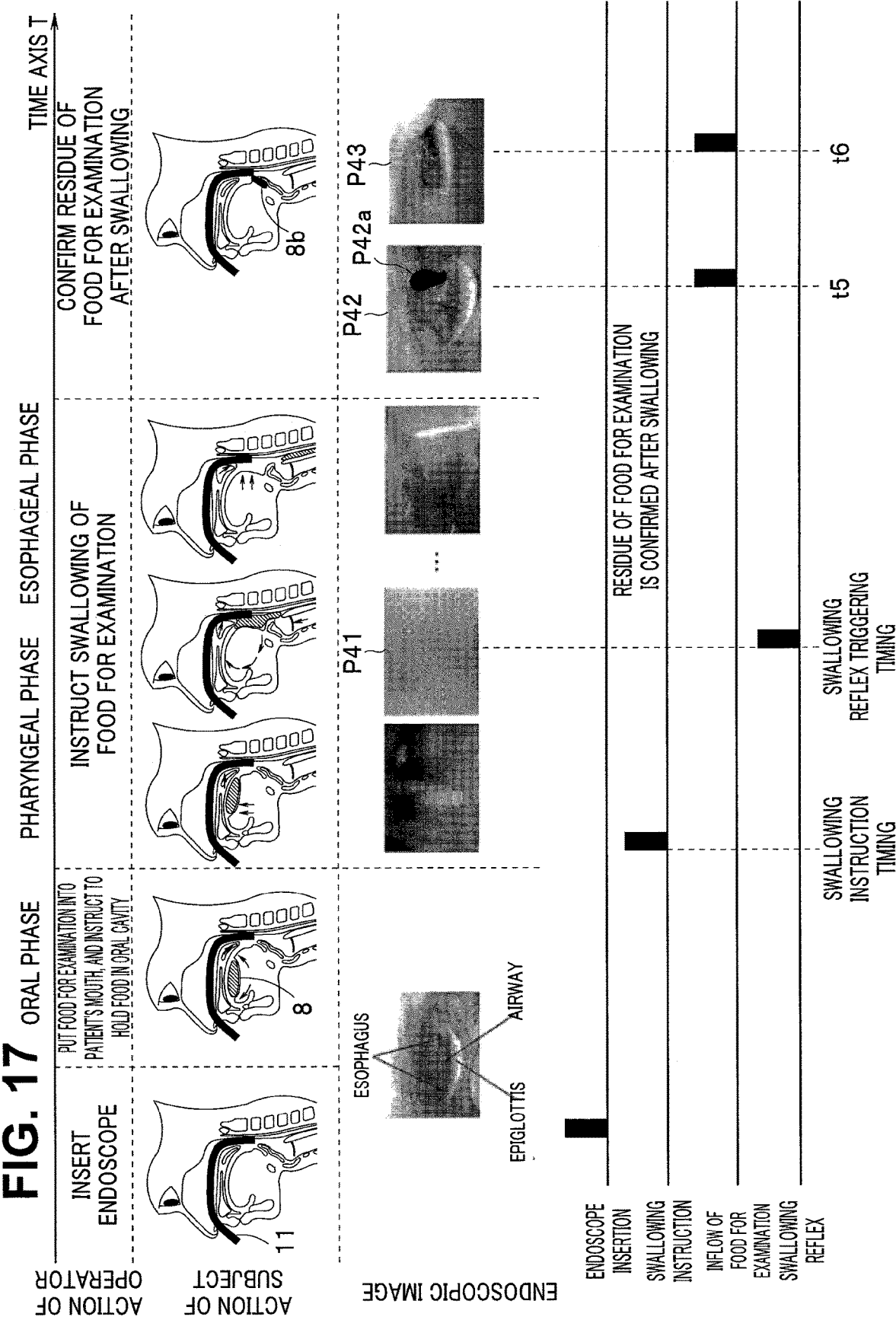
FIG. 17 is an explanatory diagram illustrating an inflow object residual disorder in the manner similar to that in FIGS. 6 and 7.
Figure 18:
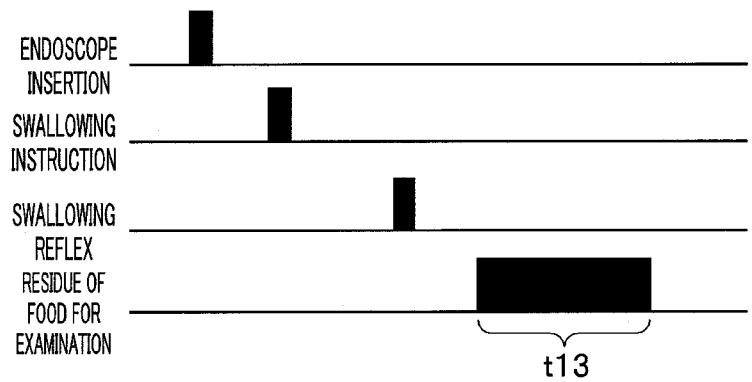
FIG. 18 is an explanatory diagram for explaining a process of determining the inflow object residual disorder in the process of determining dysphagia by the disorder determination circuit 30.

FIGS. 17 and 18 are explanatory diagrams for explaining a process of determining the inflow object residual disorder in the process of determining dysphagia by the disorder determination circuit 30. FIG. 17 illustrates an inflow object residual disorder in a manner similar to that in FIGS. 6 and 7. FIG. 18 is the diagram for explaining a method for determining the disorder level.

A column of the subject action after the end of the esophageal phase in FIG. 17 illustrates a state in which a residue 8b (solid area) of the inflow object 8 flowed into the esophagus 6 by the subject remains in the pharynx 2. In the example in FIG. 17, the residue 8b of the inflow object 8 remains in the pharynx 2 at a timing t5 after a predetermined time has elapsed since the swallowing reflex was triggered. The above is an inflow object residual disorder caused by, for example, a decrease in the swallowing ability of the subject. The disorder determination circuit 30 can detect that the residue 8b remains in the pharynx 2 based on the color of a portion P42a (solid area) in a picked-up image P42 corresponding to the residue 8b in the case above. The example in FIG. 17 illustrates a state in which the residue 8b does not remain in the pharynx 2 at a timing t6 after a predetermined time from the timing t5.

The swallowing reflex detection circuit 28 detects the swallowing reflex triggering timing by determining that an image P41 picked up by the image pickup apparatus 13 is a white-out image. The disorder determination circuit 30 detects the residue 8b by image analysis on the image picked up by the image pickup apparatus 13. When dysphagia does not occur, as illustrated in FIG. 6, no residue 8b remains in the pharynx 2 after a predetermined time from the swallowing reflex triggering timing. On the other hand, in the case of the inflow object residual disorder, as illustrated in FIG. 17, the residue 8b remains in the pharynx 2 at the timing t5 after the predetermined time from the swallowing reflex triggering timing.

The disorder determination circuit 30 reads the information on the swallowing reflex triggering timing from the timing recording memory 29, and determines whether the residue 8b remains in the pharynx 2 after the predetermined time from the swallowing reflex triggering timing. When the disorder determination circuit 30 detects that the residue 8b remains in the pharynx 2 after the predetermined time has elapsed from the swallowing reflex triggering timing, the disorder determination circuit 30 may determine that the subject has developed the inflow object residual disorder.

The disorder determination circuit 30 may determine the inflow object residual disorder and the disorder level by not only the presence or absence of the residue 8b, but also by comparing a duration that the residue 8b remains in the pharynx 2 with the determination reference time. In the case above, the disorder determination circuit 30 may detect the timing t5 at which the residue 8b remains in the pharynx 2 and a timing t6 at which the residue 8b disappears from the pharynx 2, and store the timing information on the timings t5 and t6 in the timing recording memory 29 (not illustrated).

FIG. 18 illustrates the insertion detection timing, the swallowing instruction timing, the swallowing reflex triggering timing, and the inflow object residual time by solid rectangle positions with time on the horizontal axis. The example in FIG. 18 indicates that a time t13 is the inflow object residual time during which the residue 8b remains in the pharynx 2 after the swallowing reflex triggering timing.

The disorder determination circuit 30 may read the disorder level determination reference information from the memory 30a and determine the disorder level of the inflow object residual disorder by comparing the information on the determination reference time set in the disorder level determination reference information with the inflow object residual time.

In FIG. 13, for example, assuming that the swallowing videoendoscopy is performed using an inflow object that is easy to swallow in the first setting of the determination reference time, when the t13 in FIG. 18 is 1.5 seconds, the disorder determination circuit 30 determines that the subject has a mild inflow object residual disorder, when the t13 is 5 seconds, the disorder determination circuit 30 determines that the subject has a moderate inflow object residual disorder, and when the t13 is 25 seconds, the disorder determination circuit 30 determines that the subject has a severe inflow object residual disorder. When the t13 in FIG. 18 is 0.5 seconds, the disorder determination circuit 30 determines that the inflow object residual disorder has not occurred because the remained inflow object is within the normal range.

Although it has been described that the disorder determination circuit 30 detects that the residue 8b remains in the pharynx 2, the inflow detection circuit 27 may detect the remaining and disappearance of the residue 8b and record the timing information on the detection in the timing recording memory 29.

(Display of Determination Result)

The disorder determination circuit 30 generates display information to be presented to the operator or the like based on the determination result of dysphagia. The disorder determination circuit 30 converts the generated display information into a video signal that can be displayed on the monitor 40, and then outputs the video signal to the monitor 40. Thus, on the display screen of the monitor 40, the information based on the determination result of dysphagia can be displayed. The disorder determination circuit 30 can also output the information on the determination result of dysphagia and the display information on the determination result of dysphagia to the output circuit 34.

(Operation)

Figure 19:
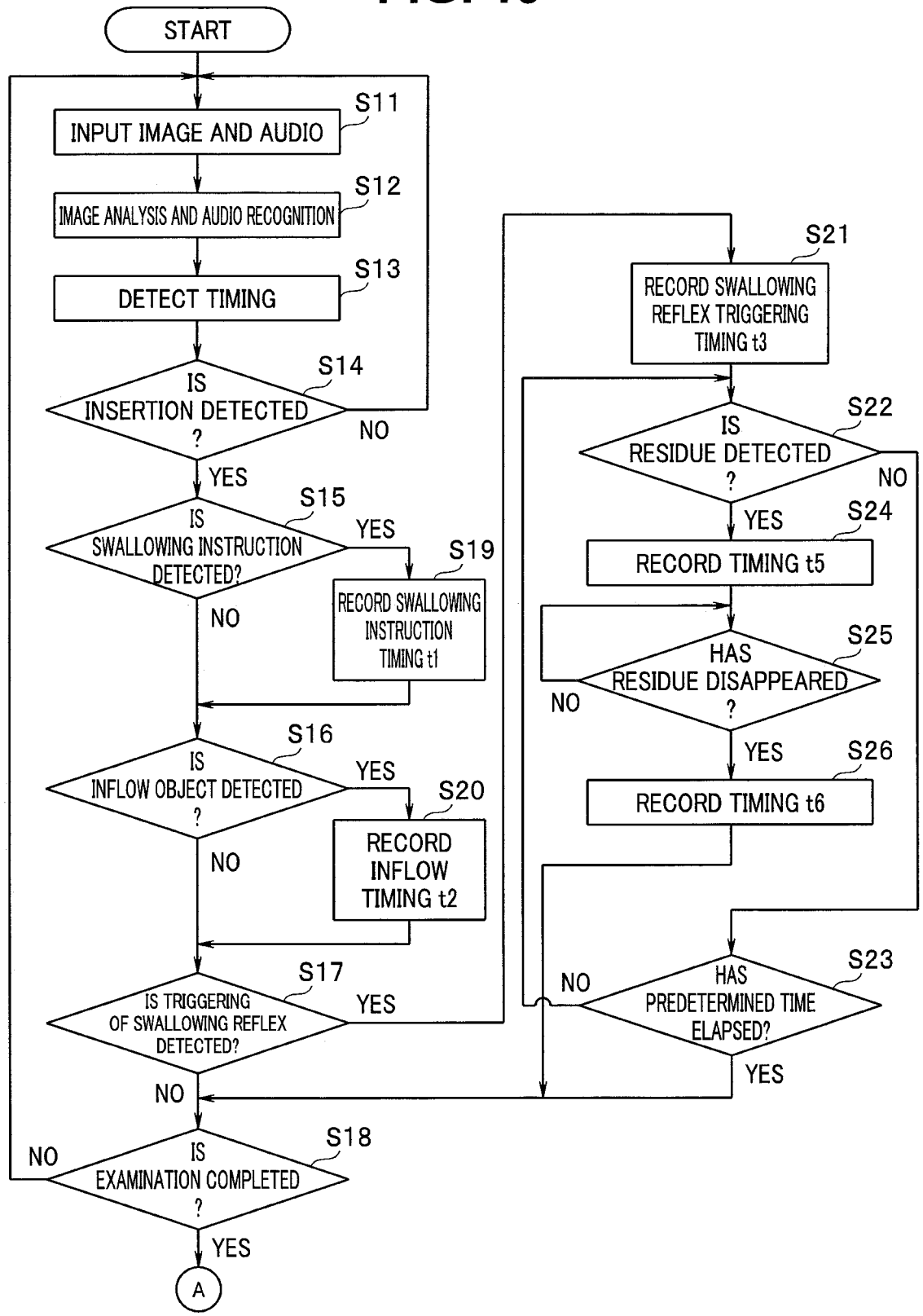
FIG. 19 is a flowchart for explaining operation of a main circuit 21.
Figure 20:
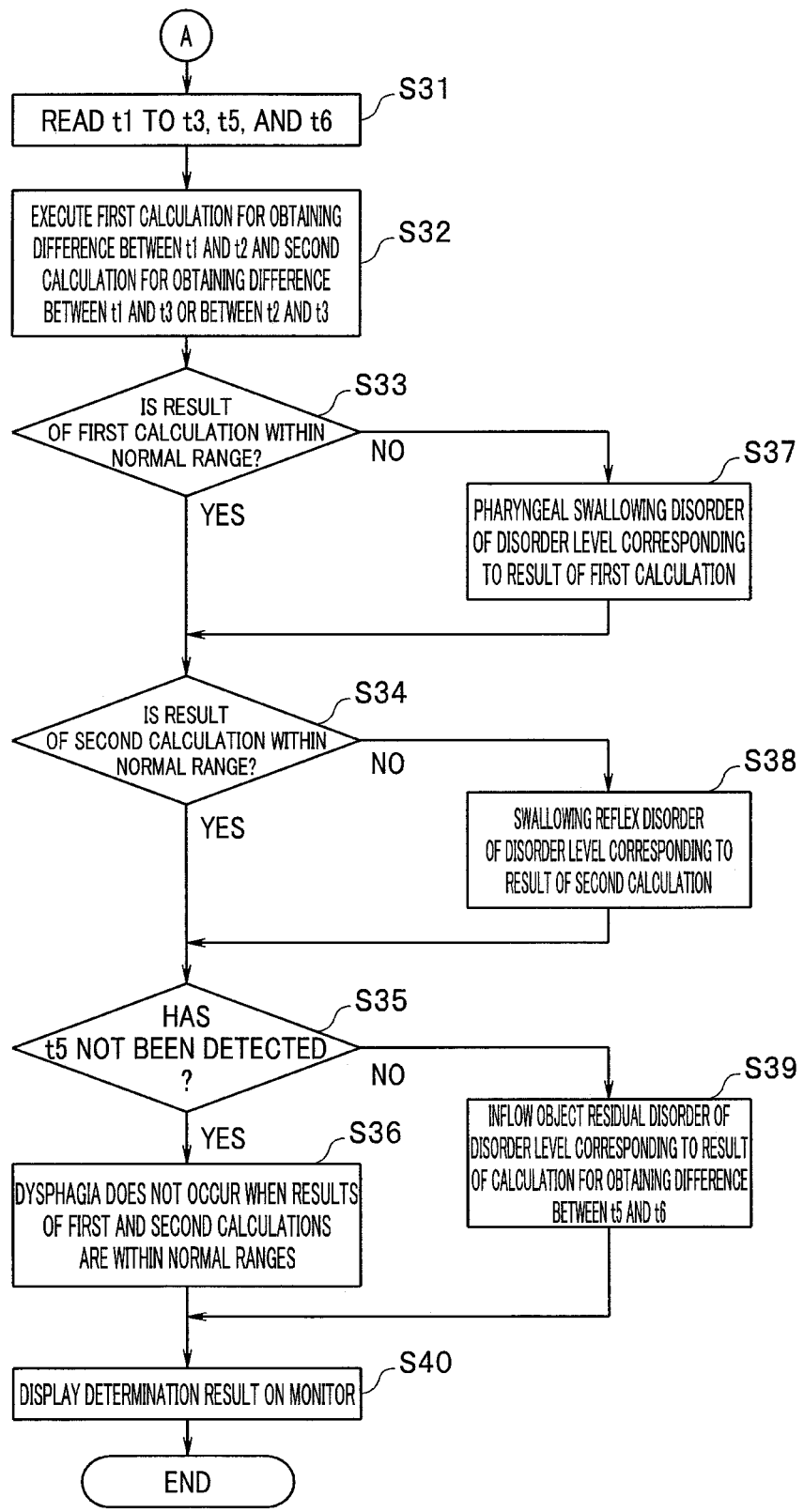
FIG. 20 is a flowchart for explaining the operation of the main circuit 21.
Figure 21:
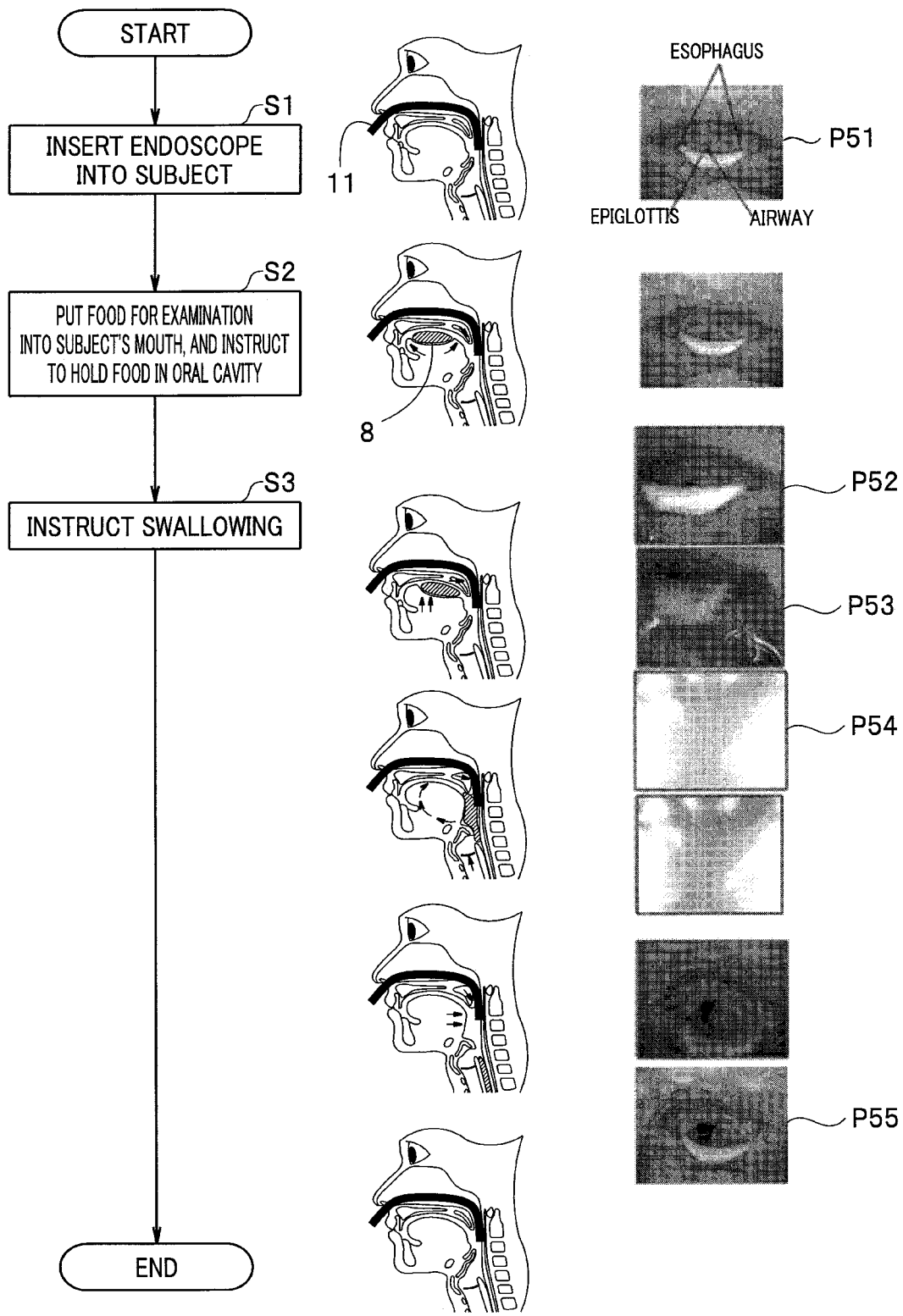
FIG. 21 is a diagram illustrating a work flow of the swallowing videoendoscopy and swallowing actions and endoscopic images (picked-up images) in a normal subject who has not developed dysphagia.

Next, operation according to the embodiment will be described with reference to FIGS. 19 to 21. FIGS. 19 and 20 are flowcharts for explaining the operation of the main circuit 21, and the same circled alphabetic letter in FIGS. 19 and 20 indicates that the circled alphabetic letter connects steps. FIG. 21 is a diagram illustrating a work flow of the swallowing videoendoscopy, swallowing actions, and endoscopic images (picked-up images) in a normal subject who has not developed dysphagia.

In step S11 of FIG. 19, the control circuit 31 in the main circuit 21 controls the illumination device 22 and the developing circuit 23 to acquire an image picked up by the image pickup apparatus 13 of the endoscope 11 (endoscopic image), and provides the acquired image to the timing detection circuit 24. The control circuit 31 also provides the audio collected by the microphone 33 to the timing detection circuit 24. In step S12, the individual circuits in the timing detection circuit 24 execute image analysis on the inputted picked-up image and audio recognition processing on the audio signal from the microphone 33.

In step S13, the individual circuits in the timing detection circuit 24 execute various kinds of timing detection. In the timing detection circuit 24, the timing detection may be executed based on an operation signal of the input operation section. Although not clearly shown in FIG. 19, steps S11 to S13 are repeated until the swallowing videoendoscopy is completed.

That is, in step S13, the swallowing instruction detection circuit 25, the endoscope insertion detection circuit 26, the inflow detection circuit 27 and the swallowing reflex detection circuit 28 in the timing detection circuit 24 detect the swallowing instruction, the insertion of the endoscope, the inflow of the inflow object 8 into the pharynx 2, and the triggering of the swallowing reflex, respectively.

In steps S14 to S17, it is determined whether the insertion, the swallowing instruction, the inflow, and the triggering of the swallowing reflex are detected, respectively. Steps S14 to S17 may be executed in any order or may be executed simultaneously.

That is, when the endoscope insertion detection circuit 26 detects the insertion of the endoscope 11, the endoscope insertion detection circuit 26 records the insertion detection timing in the timing recording memory 29. When the swallowing instruction detection circuit 25 detects the swallowing instruction, the process proceeds from step S15 to step S19. Then, the swallowing instruction detection circuit 25 records the swallowing instruction timing t1 in the timing recording memory 29. When the inflow detection circuit 27 detects the inflow of the inflow object 8, the process proceeds from step S16 to step S20. Then, the inflow detection circuit 27 records the inflow timing t2 in the timing recording memory 29. When the swallowing reflex detection circuit 28 detects the triggering of the swallowing reflex, the process proceeds from step S17 to step S21. Then, the swallowing reflex detection circuit 28 records the swallowing reflex triggering timing t3 in the timing recording memory 29.

In step S1 of FIG. 21, the operator inserts the endoscope 11 through the nasal cavity and moves the distal end portion thereof to the examination position. An image P51 shows an endoscopic image acquired by the image pickup apparatus 13 in the case above. The endoscope insertion detection circuit 26 detects that the endoscope 11 has been inserted into the nasal cavity and the distal end portion thereof has reached the examination position, and records the insertion detection timing in the timing recording memory 29.

In step S2 of FIG. 21, the operator puts the inflow object 8 such as food for examination into the subject's mouth, and instructs the subject to hold the inflow object 8 in the oral cavity. Subsequently, the operator instructs the subject to swallow the inflow object 8 (step S3). An image P52 in FIG. 21 shows an endoscopic image immediately after the swallowing instruction, and an image P53 shows that the inflow object 8 has flowed into the pharynx 2.

The swallowing instruction detection circuit 25 detects the swallowing instruction in step S15 and records the swallowing instruction timing t1 (step S19), and the inflow detection circuit 27 detects the inflow of the inflow object 8 into the pharynx 2 in step S16 and records the inflow timing t2 (step S20). Note that the example in FIG. 21 illustrates an example of a normal case in which dysphagia does not occur, and in the case that the pharyngeal swallowing disorder occurs, the inflow timing t2 may be detected earlier than the swallowing instruction timing t1.

In the example in FIG. 21, an image P54 acquired immediately after the inflow of the inflow object 8 into the pharynx 2 is a white-out image indicating that the swallowing reflex has been triggered. The swallowing reflex detection circuit 28 detects the swallowing reflex triggering in step S17 and records the swallowing reflex triggering timing t3 (step S21). Note that the example in FIG. 21 illustrates an example of a normal case in which dysphagia does not occur, and in the case that the swallowing reflex disorder occurs, the swallowing reflex triggering may be detected after a relatively long time has elapsed from the swallowing instruction timing t1 or the inflow timing t2.

In the present embodiment, dysphagia is automatically determined in the disorder determination circuit 30 based on the detected swallowing instruction timing t1, the inflow timing t2, and the swallowing reflex triggering timing t3. Therefore, the operator only needs to perform steps S1 to S3 in the swallowing videoendoscopy.

When the swallowing reflex triggering is detected in step S17, the swallowing reflex triggering timing t3 is recorded in step S21, and then whether the residue such as food for examination remains in the pharynx 2 is detected (step S22). An image P55 in FIG. 21 shows a normal example in which no inflow object remains, but in a case that the inflow object residual disorder occurs, an image in which the residue remains in the pharynx 2 is acquired.

If no residue is detected in step S22, the process proceeds to step S23 and the disorder determination circuit 30 determines whether a predetermined time has elapsed. The step S22 is repeated until the predetermined time elapses, and if no residue is detected during the period, it is determined that no residue remains, and the process proceeds to step S18.

When a residue is detected in the pharynx 2, the disorder determination circuit 30 records a detection timing t5 in the next step S24. Subsequently, the disorder determination circuit 30 determines whether the residue in the pharynx 2 has disappeared (step S25). When the disorder determination circuit 30 detects the disappearance of the residue, the disorder determination circuit 30 records a detection timing t6 of the disappearance (step S26), and the process proceeds to step S18.

In step S18, the control circuit 31 determines whether the examination is completed. For example, the control circuit 31 may determine that the examination is completed when a predetermined examination time has elapsed from any of the timings t1 to t3. Alternatively, the control circuit 31 may determine the completion of the examination by the operation of an input operation section (not illustrated) by the operator. If the control circuit 31 determines that the examination is not completed, the process returns to step S11, and if the control circuit 31 determines that the examination is completed, the process proceeds to step S31.

In step S31, the disorder determination circuit 30 reads information on the timings t1 to t3, t5, and t6 from the timing recording memory 29. The disorder determination circuit 30 executes a first calculation for obtaining a difference between t1 and t2, and executes a second calculation for obtaining a difference between t1 and t3 or a difference between t2 and t3 (step S32).

In step S33, the disorder determination circuit 30 determines whether the result of the first calculation is within the normal range for the pharyngeal swallowing. For example, the disorder determination circuit 30 reads the disorder level determination reference information from the memory 30a and determines the presence or absence and the level of the pharyngeal swallowing disorder by comparing the information on the determination reference time included in the disorder level determination reference information with the first calculation result. For example, in the case in which the determination reference time defined by the information on the determination reference time included in the disorder level determination reference information is the first setting, when the first calculation result is 0.5 seconds, the disorder determination circuit 30 determines that the first calculation result is within the normal range and pharyngeal swallowing disorder has not occurred, and the process proceeds to step S34. For example, when the first calculation result is 25 seconds, the disorder determination circuit 30 determines that a severe pharyngeal swallowing disorder has occurred based on the first calculation result (step S37), and then the process proceeds to step S34.

In step S34, the disorder determination circuit 30 determines whether the calculation result of the second calculation is within the normal range for the swallowing reflex triggering. For example, the disorder determination circuit 30 determines the presence or absence and the level of the swallowing reflex disorder by comparing the information on the determination reference time set in the disorder level determination reference information with the second calculation result. For example, in the case in which the determination reference time is the first setting, when the second calculation result is 0.5 seconds, the disorder determination circuit 30 determines that the second calculation result is within the normal range and swallowing reflex disorder has not occurred. Then, the process proceeds to step S35. For example, when the first calculation result is 25 seconds, the disorder determination circuit 30 determines that a severe swallowing reflex disorder has occurred based on the second calculation result (step S38), and then the process proceeds to step S35.

In step S35, the disorder determination circuit 30 determines whether the timing t5 has been detected. When the disorder determination circuit 30 determines that the timing t5 has not been detected because no residue remains in the pharynx 2, the process may proceed to step S36. When the first and second calculation results are within the normal ranges, the disorder determination circuit 30 determines that dysphagia has not occurred, and the process proceeds to step S40.

When the timings t5 and t6 are detected, the disorder determination circuit 30 determines the presence or absence and the level of the inflow object residual disorder by comparing the information on the determination reference time set in the disorder level determination reference information with the difference between t5 and t6. For example, in the case in which the determination reference time is the first setting, when the difference between t5 and t6 is 0.5 seconds, the disorder determination circuit 30 may determine that the swallowing reflex disorder has not occurred. For example, when the difference between t5 and t6 is 25 seconds, the disorder determination circuit 30 may determine that a severe inflow object residual disorder has occurred (step S39), and then the process may proceed to step S40.

Based on the determination results of steps S37, S38, S36, and S39, the disorder determination circuit 30 generates display information for presenting the determination result of dysphagia to the operator or the like, converts the generated display information into a video signal that can be displayed on the monitor 40, and then outputs the video signal to the monitor 40. Thus, the information based on the determination result of dysphagia is displayed on the display screen of the monitor 40 (step S40).

In the above description, an example has been described in which three timings of the swallowing instruction timing, the inflow timing, and the swallowing reflex triggering timing are obtained to determine the pharyngeal swallowing disorder, the swallowing reflex disorder, and the inflow object residual disorder. However, in a case in which any one of the disorders is needed to determine, two of the three timings may be obtained.

As described above, in the present embodiment, at least two of the swallowing instruction timing, the inflow timing, and the swallowing reflex triggering timing are detected using the image information, the audio information, and the like acquired by the image pickup apparatus and the microphone. Thus, based on the time relationship between the respective timings, it is possible to automatically obtain the diagnostic results such as the pharyngeal swallowing disorder, the swallowing reflex disorder, and the inflow object residual disorder. Thus, even a person who is not an operator skilled in the swallowing videoendoscopy can make a more objective and quantitative diagnosis.

In addition, in the present embodiment, it is possible to output the information on the swallowing instruction timing, the inflow timing, and the swallowing reflex triggering timing, and it is also possible to use such kinds of timing information in other devices.

Second Embodiment

Figure 22:
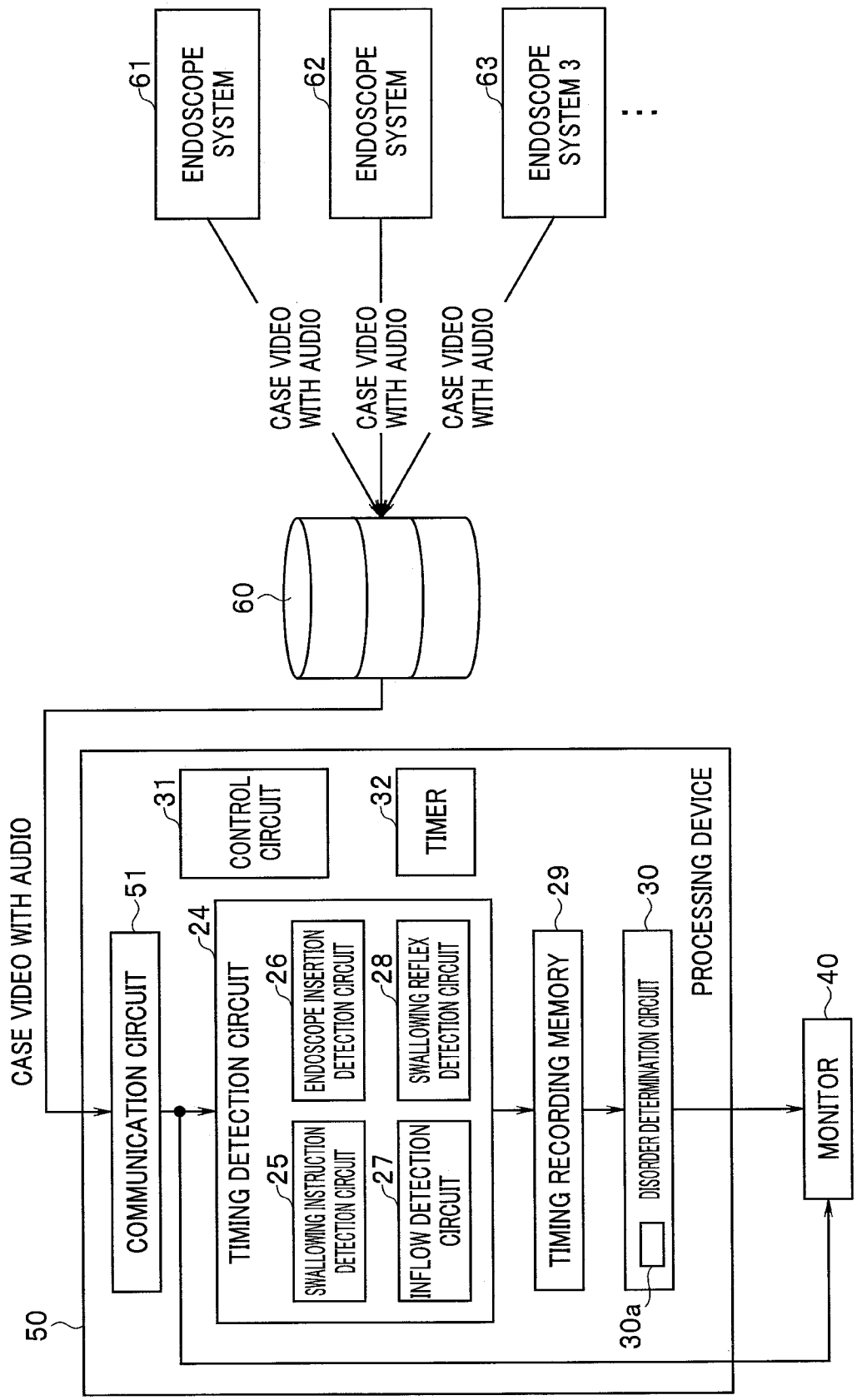
FIG. 22 is a block diagram illustrating another embodiment.

FIG. 22 is a block diagram illustrating another embodiment. In FIG. 22, the same constituent elements as those in FIG. 1 are denoted by the same reference numerals, and descriptions thereof will be omitted. In the first embodiment, an example in which the swallowing videoendoscopy system is applied to one endoscope system has been described. The present embodiment illustrates an example applied to a plurality of endoscope systems.

FIG. 22 illustrates an endoscope system 61, a database 60, and a processing device 50, which are located far away from each other and can communicate with each other. When the endoscope system 61 and the processing device 50 directly communicate with each other, the database 60 may be omitted.

Each of the endoscope systems 61, 62, . . . has an image pickup function, an audio collecting function, a recording function for recording picked-up images and audio, and a communication function for transmitting recorded information, which are necessary for swallowing videoendoscopy. For example, each of the endoscope systems 61, 62, . . . can include a general nasal endoscope, a microphone, and a video processor that processes images acquired by the nasal endoscope and audio collected by the microphone. That is, each of the endoscope systems 61, 62, . . . can perform swallowing videoendoscopy according to the work flow in FIG. 21, record images and audio acquired from the swallowing videoendoscopy, and transmit the recorded images and audio to the database 60 as a case video with audio.

The database 60 is composed of predetermined storage devices, and can record the case videos with audio transmitted from the endoscope systems 61, 62, . . . and transfer the case videos with audio to the processing device 50.

The processing device 50 may be configured by a computer system using, for example, a personal computer or a tablet terminal. The processing device 50 includes a communication circuit 51. The communication circuit 51 may be configured to enable communication such as wireless communication using a wireless LAN such as Wi-Fi or Bluetooth, or wired communication using a LAN cable. The communication circuit 51 can receive the case video with audio from the database 60 and supply the case video with audio to a timing detection circuit 24.

In FIG. 22, the configurations of a timing detection circuit 24, a timing recording memory 29, and a disorder determination circuit 30 are the same as those in FIG. 1. Based on the video included in the case video with audio, an endoscope insertion detection circuit 26 detects an insertion detection timing, a swallowing instruction detection circuit 25 detects a swallowing instruction timing, an inflow detection circuit 27 detects an inflow timing of an inflow object, and a swallowing reflex detection circuit 28 detects a swallowing reflex triggering timing.

Other functions are the same as those of the first embodiment.

In the present embodiment, the processing device 50 can determine dysphagia by using case videos with audio acquired from the swallowing videoendoscopy at distant locations.

In order to efficiently perform swallowing diagnoses by a small number of doctors, for example, a number of swallowing videoendoscopy performed by technicians called speech-language pathologists (SLPs) increases in the United States. The SLP visits the patient to perform swallowing videoendoscopy, and uploads a recorded case video with audio to a database. The doctor downloads the case video with audio from the database and makes diagnosis while watching the case video with audio.

In the present embodiment, the case video with audio is downloaded from the database, and instead of the doctor, the processing device 50 detects the swallowing instruction timing, the inflow timing, and the swallowing reflex triggering timing to quantitatively evaluate the pharyngeal swallowing disorder, the swallowing reflex disorder, and the inflow object residual disorder, thereby providing diagnostic support.

As described above, in the present embodiment, diagnosis of dysphagia can be made using an acquired case video with audio of swallowing videoendoscopy at a distant location, so that objective, quantitative, and effective diagnostic support for the swallowing videoendoscopy can be provided, and the swallowing videoendoscopy can be made simpler.

The present invention is not limited to the above-described embodiments as they are, and can be embodied by modifying the constituent elements without departing from the scope of the gist of the present invention at the implementation stage. In addition, various inventions can be formed by appropriately combining the plurality of constituent elements disclosed in the above embodiments. For example, some of all the constituent elements illustrated in the embodiments may be deleted. Furthermore, the constituent elements in different embodiments may be appropriately combined.

What is claimed is:

1. An examination device comprising:
a processor comprising hardware, wherein the processor is configured to:
receive input signal over time;
receive image signal of a plurality of images captured by an endoscope over time;
process the plurality of images to detect an image of the plurality of images having at least a predetermined number of pixels having a red hue as an examination position image captured by the endoscope at a predetermined examination position;
after detecting the examination position image, perform at least two of:
process the input signal to detect a swallowing instruction timing at which a swallowing instruction is captured;
process the plurality of images to detect an inflow timing at which an image of the plurality of images having pixels that cover at least a predetermined area having a color influenced by a color of an inflow object during a swallowing action is captured; and process the plurality of images to detect a swallowing reflex triggering timing, occurring after the inflow timing, at which a white-out image of the plurality of images having an average pixel value that is at least a predetermined brightness and/or having a number of edge portions that is equal to or less than a predetermined threshold is captured.

2. The examination device according to claim 1,
wherein the processor is configured to determine presence of dysphagia of the subject based on the at least two of the swallowing instruction timing, the inflow timing and the swallowing reflex triggering timing detected.

3. The examination device according to claim 1,
wherein the processor is configured to:
   process a voice of an operator or an operation signal generated by operation of the operator, as the input signal, to detect the swallowing instruction timing; and
   process an output of a contact sensor configured to detect a movement of a living tissue due to the swallowing action to detect the swallowing reflex triggering timing.

4. The examination device according to claim 3,
wherein the processor is configured to:
   detect an insertion detection timing at which the endoscope reaches a position at which an image of the swallowing action is able to be picked up; and
   after the insertion detection timing, perform the at least two of process the input signal to detect the swallowing instruction timing, process the plurality of images to detect the inflow timing and process the plurality of images to detect the swallowing reflex triggering timing.

5. The examination device according to claim 2,
wherein the processor is configured to determine presence of a pharyngeal swallowing disorder based on a relationship between the inflow timing and the swallowing instruction timing.

6. The examination device according to claim 4,
wherein the processor is configured to determine presence of a swallowing reflex disorder based on a relationship between the inflow timing and the swallowing reflex triggering timing or a relationship between the swallowing instruction timing and the swallowing reflex triggering timing.

7. The examination device according to claim 2,
wherein, after the swallowing reflex triggering timing, the processor is configured to determine an inflow object residual disorder by detecting the inflow object remaining in a pharynx.

8. The examination device according to claim 1,
wherein the processor is configured to control a monitor to display information based on one or more of the swallowing instruction timing, the inflow timing and the swallowing reflex triggering timing.

9. The examination device according to claim 2,
wherein the processor is configured to control a monitor to display information based on a determination result of the presence of dysphagia.

10. The examination device according to claim 2, further comprising:
a memory configured to store disorder level determination reference information that serves as a reference for disorder determination,
wherein the processor is configured to determine a disorder level of the dysphagia based on the at least two of the swallowing instruction timing, the inflow timing and the swallow reflex triggering timing, and information on a determination reference time included in the disorder level determination reference information stored in the memory.

11. The examination device according to claim 10,
wherein the disorder level determination reference information includes information on the determination reference time corresponding to ease of swallowing the inflow object.

12. An endoscope system comprising:
an endoscope, in swallowing videoendoscopy in which an inflow object is given to a subject and a swallowing action is observed, configured to be inserted into the subject, pick up a plurality of images over time and output the plurality of images;
a processor comprising hardware, wherein the processor is configured to:
   receive input signal over time;
   receive image signal of the plurality of images captured by the endoscope over time;
   process the plurality of images to detect an image of the plurality of images having at least a predetermined number of pixels having a red hue as an examination position image captured by the endoscope at a predetermined examination position;
   after detecting the examination position image, perform at least two of:
      process the input signal to detect a swallowing instruction timing at which a swallowing instruction is captured;
      process the plurality of images to detect an inflow timing at which an image of the plurality of images having pixels that cover at least a predetermined area having a color influenced by a color of an inflow object during the swallowing action is captured; and
      process the plurality of images to detect a swallowing reflex triggering timing, occurring after the inflow timing, at which a white-out image of the plurality of images having an average pixel value that is at least a predetermined brightness and/or having a number of edge portions that is equal to or less than a predetermined threshold is captured.

13. The endoscope system according to claim 12,
wherein the processor is further configured to determine dysphagia of the subject based on the at least two of the swallowing instruction timing, the inflow timing and the swallowing reflex triggering timing detected.

14. An examination method comprising
receiving input signal over time;
receiving image signal of a plurality of images captured by an endoscope over time;
processing the plurality of images to detect an image of the plurality of images having at least a predetermined number of pixels having a red hue as an examination position image captured by the endoscope at a predetermined examination position;
after detecting the examination position image, perform at least two of:
   processing the input signal to detect a swallowing instruction timing at which a swallowing instruction is capture;
   processing the plurality of images to detect an inflow timing at which an image of the plurality of images having pixels that cover at least a predetermined area having a color influenced by a color of an inflow object during a swallowing action is captured; and processing the plurality of images to detect a swallowing reflex triggering timing, occurring after the inflow timing, at which a white-out image of the plurality of images having an average pixel value that is at least a predetermined brightness and/or having a number of edge portions that is equal to or less than a predetermined threshold is captured.

15. The examination method according to claim 14, further comprising:

determining dysphagia of a subject based on the at least two of the swallowing instruction timing, the inflow timing and the swallowing reflex triggering timing detected.

16. The endoscope system according to claim 12, wherein the processor is configured to:

process a voice of an operator or an operation signal generated by operation of the operator, as the input signal, to detect the swallowing instruction timing; and process an output of a contact sensor configured to detect a movement of a living tissue due to the swallowing action to detect the swallowing reflex triggering timing.

17. The endoscope system according to claim 16, wherein the processor is configured to:

detect an insertion detection timing at which the endoscope reaches a position at which an image of the swallowing action is able to be picked up; and after the insertion detection timing, perform the at least two of process the input signal to detect the swallowing instruction timing, process the plurality of images to detect the inflow timing and process the plurality of images to detect the swallowing reflex triggering timing.

18. The endoscope system according to claim 13, wherein the processor is configured to determine presence of a pharyngeal swallowing disorder based on a relationship between the inflow timing and the swallowing instruction timing.

19. The endoscope system according to claim 17, wherein the processor is configured to determine presence of a swallowing reflex disorder based on a relationship between the inflow timing and the swallowing reflex triggering timing or a relationship between the insertion detection timing and the swallowing reflex triggering timing.

20. The endoscope system according to claim 13, wherein, after the swallowing reflex triggering timing, the processor is configured to determine an inflow object residual disorder by detecting the inflow object remaining in a pharynx.

* * * * *